United States Patent [19]

Scott et al.

[11] Patent Number: 5,616,615

[45] Date of Patent: *Apr. 1, 1997

[54] ENAMINONE ESTERS

[75] Inventors: Kenneth R. Scott, Silver Spring; Jesse M. Nicholson, Upper Marlboro; Ivan O. Edafiogho, Oxon Hill, all of Md.

[73] Assignee: Howard University, Washington, D.C.

[ * ] Notice: The term of this patent shall not extend beyond the expiration date of Pat. No. 5,468,725.

[21] Appl. No.: 487,341

[22] Filed: Jun. 7, 1995

Related U.S. Application Data

[60] Division of Ser. No. 24,970, Mar. 2, 1993, Pat. No. 5,468,775, which is a continuation-in-part of Ser. No. 844,068, Mar. 2, 1992, abandoned.

[51] Int. Cl.$^6$ .................................................. A61K 31/24
[52] U.S. Cl. ........................... 514/511; 560/21; 560/34; 560/35; 560/45; 560/47; 560/48
[58] Field of Search ............................. 514/541; 560/21, 560/34, 35, 45, 47, 48

[56] References Cited

U.S. PATENT DOCUMENTS

| | | | |
|---|---|---|---|
| 3,969,409 | 7/1976 | Miyano et al. | 260/570.5 |
| 4,515,982 | 5/1985 | Lechtken et al. | 560/125 |
| 5,468,775 | 11/1995 | Scott | 514/541 |

FOREIGN PATENT DOCUMENTS

| | | |
|---|---|---|
| 50-46645 | 4/1975 | Japan. |
| 57-116048 | 7/1982 | Japan. |

OTHER PUBLICATIONS

Edafiogho, J. Med. Chem., 35, pp. 2798–2805 (Jul. 24, 1992).

"Condensation of Diethyl Malonate with Methyl Vinyl Ketone"; Thomas A. Spencer, Marshall D. Newton, and Steven W. Baldwin; *The Journal Of Organic Chemistry*; vol. 29, pp. 787–789; Jan.–Apr. 1964.

"Mechanism of Enamine Reactions. II. The Hydrolysis of Tertiary Enamines"; E.J. Stamhuis and W. Maas; *Journal of Organic Chemistry*; vol. 30, pp. 2156–2160; Jul. 1965.

"Mechanism of Enamine Reactions. III. The Basicity of Tertiary Enamines"; E.J. Stamhuis, W. Maas, and Hans Wynberg; *Journal of Organic Chemistry*, vol. 30, pp. 2160–2163; Jul. 1965.

"Mechanism of Enamine Hydrolysis"; Paula Y. Sollenberger and R. Bruce Martin; *J. Am. Chem. Soc.*, pp. 4261–4270; Jul. 15, 1970.

"Catalysis by Molecular Sieves in the Preparation of Ketimines and Enamines"; Kazuo Taguchi and F.H. Westheimer; *J. Org. Chem.*, vol. 36, No. 11, pp. 1570–1572, 1971.

"Heterocyclic Syntheses via the Intramolecular Acylation of Enamines Derived from Amino Acids"; Richard J. Friary, Sr. Jeanne M. Gilligan, Richard P. Szajewski, Kenneth J. Falci, and Richard W. Franck; *The Journal Of Organic Chemistry*; vol. 38, pp. 3487–3491; Sep.–Dec. 1973.

"Reaction of Substituted Sulfenes with N,N–Disubstituted α–Amino–methyleneketones. I. Synthesis of N,N–Disubstituted cis– and trans–4–Amino–3,4,5,6,7,8–hexahydro–3–phenyl–1,2–benzoxathiin 2,2–Dioxides"; Alberto Bargagna, Gaetano Bignardi, Pietro Schenone and Mario Longobardi; *Journal of Heterocyclic Chem.*, pp. 839–843; Jul.–Aug. 1983.

"Reaction of Ketenes with N,N–Disubstituted α–Aminomethyleneketones. SVI. Synthesis of N,N–Disubstituted 4–Amino–5,6–tetramethylene–3–phenyl–2–pyranones"; Alberto Bargagna, Pietro Schenone and Mario Longobardi; *Journal of Heterocyclic Chem.*, pp. 1471–1473; Nov.–Dec. 1985.

"Alkylation of Enaminone Esters"; I.O. Edafiogho, Ph.D., MBIM, C. Chem., MRSC, MPSN; College of Heatlh Sciences, Usmanu Danfodiyo University; *Pharmacy World Journal*, vol. 7, No. 1, pp. 20–32; Jan.–Mar. 1990.

"Some Pharmacological Effects of an Enaminone Ester of Isolated Rat Uterus"; I.O. Edafigho, B.Y. Muhammad, and P.C. Unekwe; *Nigerian Journal of Basic and Applied Sciences* (1989) 3: 35–40.

"Nuclear Magnetic Resonance Studies of Anticonvulsant Enaminones"; Ivan O. Edafiogho, Jacqueline A. Moore, Mariano S. Alexander, and K.R. Scott; *J. of Pharm. Sci.*, Vo. 83, No. 8, Aug. 1994.

"Synthesis and Anticonvulsant Activity of Enaminones. 3. Investigations on 4'–, 3'–, and 2'–Substituted and Polysubstituted Anilino Compounds, Sodium Channel Binding Studies, and Toxicity Evaluations"; K.R. Scott, Gary O. Rankin, James P. Stables, Mariano, S. Alexander, Ivan O. Edafiogho, Vida A. Farrar, Kymberle R. Kolen, Jacqueline A. Moore, Lyndia D. Sims, and Ahn D. Tonnu; *J. Med. Chem.* 1995, 38, 4033–4043.

"A New Synthesis of 2–Alkyl and 2–Acylketones"; Gilbert Stork, Ross Terrell and Jacob Szmuszkovicz; *Journal of the American Chemical Society*; vol. 76, pp. 2029–2030; Apr. 5, 1954.

"Some Basically Substituted Acrylic Acid Derivatives"; Edgar A. Steck; *J. Org. Chem.*, vol. 27, pp. 306–308, 1962.

(List continued on next page.)

*Primary Examiner*—Michael L. Shippen
*Attorney, Agent, or Firm*—Kenyon & Kenyon

[57] ABSTRACT

The present invention concerns enaminones having the formula:

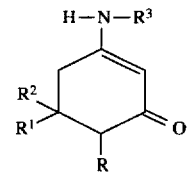

wherein R is $COOCH_3$; $R^1$ is $CH_3$; $R^2$ is H; and $R^3$ is selected from the group consisting of $C_6H_4(p-Cl)$ and $CH_2C_6H_5$.

4 Claims, 2 Drawing Sheets

OTHER PUBLICATIONS

"The Enamine Alkylation and Acylation of Carbonyl Compounds"; Gilbert Stork, A. Brizzolara, H. Landesman, J. Szmuskovicz and R. Terrell; *Journal of the American Chemical Society*; vol. 85, pp. 207–222; Jan. 20, 1963.

"Enamine Derivatives of Malonic Acid with Pharmacologic Activities"; Arthur A. Santilli, William F. Bruce and T.S. Osdene; *J. Med. Chem.*, vol. 7, pp. 68–72; Jan. 1964.

"Reaction of N,N–Disubstituted α–Aminomethyleneketones with Tosyl Isocyanate; Synthesis of amino–disubstituted 2–acyl–3–amino–N–tosylpropenamides, N,N–(3–amino–1–alkyl–2–proenylidene) and N,N–[2–(aminomethylene)cyclohexylidene]tosylamides"; G. Romussi, P. Parodi, G. Bignardi, G. Menozzi and P. Schenone; *Il Farmaco Ed. Sc.*, vol. 41, pp. 539–547; 1986.

"Mechanism of Hydrolysis and Structure – Stability Relationship of Enaminones as Potential Prodrugs of Model Primary Amines"; Vijay H. Naringrekar and Valentino J. Stella; *Journal of Pharmaceutical Sciences*; vol. 79, No. 2, pp. 138–146; Feb. 1990.

*Chemical Abstracts*; Mar. 1, 1993; vol. 118, No. 9, p. 84.

"Pharmacological Studies on Centrally–Acting Drugs Belonging to Enaminone Mannich Bases"; Yoshitoshi Kase, Katsuko Masaki, Takeshi Miyata, Kazuo Takahama, Masaru Saita and Go Kito, Dept. Of Chemico–Pharmacology, Faculty of Pharm. Sciences, University of Kumamoto, Kumamoto, Japan; *Jap. J. Of Pharmacology*, vol. 24 (Abstract 127), p. 85 (Proceedings – 47th General Meeting Japanese Pharmacological Socitey; Mar. 31–Apr. 2, 1974, Tokyo, Japan).

"Pharmacological Studies on Centrally–Acting Drugs Belonging to Enaminone Mannich Bases. II. Pharmacology OF MK 1–203 and 1–907, New Potent Analgesics"; Yoshitoshi Kase, Masaru Saita, Katsuko Masaki and Takeshi Miyata; Dept of Chemico–Pharmacology, Faculty of Pharmaceutical Sciences, University of Kumamoto; Kumamoto, Japan; *Jap. J. Of Pharmacology*, vol. 24 (Abstract 128), p. 86 (Proceedings – 47th General Meeting Japanese Pharmacological Society; Mar. 31–Apr. 2, 1974, Tokyo, Japan).

"The Synthesis of 1H–Pyrroles"; Gerritt Bean; Chapter 2 in *Heterocyclic Chemistry*, vol. 48, Part 1, J. Wiley & Sons, New York, NY, 1992.

J. Med. Chem., 1992, 35, 2798–2805; *Synthesis and Anticonvulsant Activity of Enaminones;* Ivan O. Edafiogho, Christine N. Hinko, Hyejung Chang, Jacqueline A. Moore, Dianna Mulzac, Jesse M. Nicholson, and K. R. Scott.

Epilepsia, vol. 34, No. 6: 1141–1146, 1993; *Profile of Anticonvulsant Activity and Minimal Toxicity of Methyyl 4–[(p–Chlorophenyl)amino]–6–Methyl–2–Oxo–Cyclohex–3–En–1–Oate and Some Prototype Antiepileptic Drugs in Mice and Rats;* Dianna Mulzac and Kenneth R. Scott.

J. Med. Chem., vol. 36, No. 14, 1947–1955; *Synthesis and Anticonvulsant Activity of Enaminones.2.Further Structure–Activity Correlations;* K. R. Scott, Ivan O. Edafiogho, Erica L. Richardson, Vida A. Farrar, Jacqueline A. Moore, Elizabeth I. Tietz, Christine N. Hinko, Hyejung Chang, Afif El–Assadi, and Jesse M. Nicholson (1993).

Current Medicinal Chemistry, 1994, 1, 159–175; *Anticonvulsant Enaminones: With Emphasis on Methyl 4–[(P.–Chlorohenyl)Amino]–6–Methyl–2–Oxocyclohex–3–En–1–Oate (ADD 196022);* I. O. Edafiogho, M. S. Alexander, J. A. Moore, V. A. Farrar and K. R. Scott.

* = SIGNIFICANTLY DIFFERENT THAN CONTROLS (0 mg/kg), p < 0.05

PHENYTOIN

12

27

DEACTIVATED BENZYLAMINE

ACTIVATED ANILINE

ENAMINONE ESTERS

This is a division of application Ser. No. 08/024,970 filed 2 Mar. 1993, now U.S. Pat. No. 5,468,775 which is a continuation-in-part of application Ser. No. 07/844,068 filed 2 Mar. 1992, now abandoned.

FIELD OF THE INVENTION

This invention relates to novel synthetic organic compounds having significant central nervous system activity. More particularly, this invention relates to novel enaminone esters and enaminone amides and to their methods of synthesis. Of particular interest are the cyclized enaminone esters, which have markedly potent anticonvulsant activity, with only slight toxicity.

BACKGROUND OF THE INVENTION

Enaminones are a class of enamines, i.e., $\alpha,\beta$-unsaturated amines analogous to enols. Enamines are Schiff bases, and are highly unstable in aqueous solutions. As such, enamines are used as potential prodrugs (agents which yield an amine on hydrolysis) providing a lipophilic, but acid-labile, carrier group to the active pharmacophore.

Enaminones are formed between a primary amine and a $\beta$-dicarbonyl compound, often referred to as vinylogous amides, in which the amino group is linked through a carbon-carbon double bond to a keto group. These compounds are well known; see, *The Chemistry of Enamines*, S. F. Dyke, Ed., Cambridge University Press, Cambridge, U.K. (1973); *Enamines: Synthesis, Structure and Reactions*, A. G. Cook, Ed., Marcel Dekker, New York (1969).

Enaminones are stabilized relative to enamines of monocarbonyl compounds probably due to intramolecular hydrogen bonding derived from $\beta$-diketones, such as acetylacetone, and such derivatives have found usefulness as prodrugs of amines. The physicochemical properties, uses, and the hydrolysis of enamines under a variety of conditions are also well known: P. Y. Sollenberger, R. B. Martin, *J. Am. Chem. Soc.* (1970) Vol. 94, 4261–4270; J. K. Coward, T. C. Bruice, *J. Am. Chem. Soc.* (1969), Vol. 91, 5329–5339; K. Dixon, J. V. Greenhill, *J. Chem. Soc., Perkin Trans.* 2 (1974), Vol. 2, 164–168; E. J. Stamhuis, W. Mass, *J. Org. Chem.* (1965), Vol. 30, 2156–2160; J. Kavalek, El-Bahei Said, V. Sterba, *Collect. Czech. Chem. Commun.* (1978) Vol. 43, 2732–2739; L. R. Fedor, *Int. J. Pharm.* (1984), Vol. 22, 197–205; J. D. Loosen, H. Bundgaard, *Arch. Pharm. Chem. Sci., Ed.* (1986), Vol. 14, 53–63; V. H. Naringrekar, V. J. Stella, *J. Pharm. Sci.* (1990), Vol. 79, 138–146.

Research related to enaminones has been generally limited to the stability of these compounds and their ability to yield the primary or secondary amine on hydrolysis. Naringrekar and Stella recently reported disappointing results in the use of enaminones as prodrugs. There it was reported that enaminones formed between amines and cyclic 1,3-dicarbonyl compounds were significantly more stable than acyclic analogs. Two articles did cite the potential use of enaminones for biological purposes (G. Romussi, B. Parodi, G. Bignardi, G. Menozzi, P. Schenone, *Il Farmaco-Ed. Sc.* (1986) Vol. 41, 539–547; Y. Kase, M. Saita, K. Takahama, K. Masaki, T. Miyata,—*Jap. J. Pharmacol.* (1974) Vol. 24, S127–S128). In the former reference, enaminones were evaluated for hypoglycemic effectiveness. However, the authors reported no interesting results. In the latter reference, a Japanese abstract, the authors reported MK 1-203 (5,5-dimethyl-3-(o-chloro)phenylamino-2-(N-piperidinylmethyl)cyclohex-2-ene-1-one), and MK 1–907 (5,5-dimethyl-3-(m-methoxy)phenyl-2-N-methyl-N-phenethylaminomethylcyclohex-2-ene-1-one), each of which were potent analgesics with morphine-like, as well as anticonvulsant and papaverine-like, actions. No further data was provided nor any subsequent information was cited from their laboratories. Significantly, none of the reports suggest the use of enaminones as central nervous system agents, which may be effective for a variety of disorders, notably epilepsy, parkinsonism, Huntington's chorea and Alzheimer's disease.

SUMMARY OF THE INVENTION

Figure 1A:
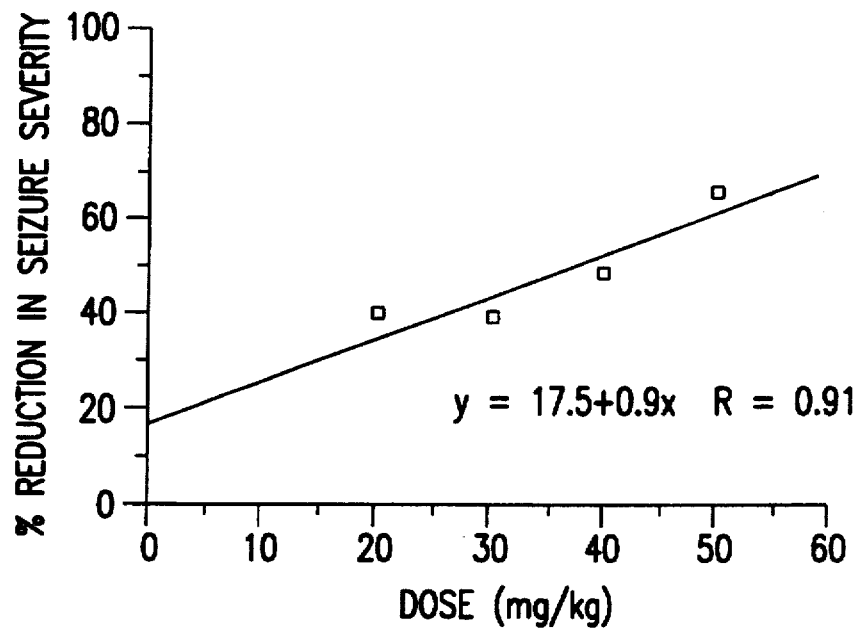
FIGS. 1A and 1B show the reduction in seizure severity provided by an enaminone of the present invention in Corneal Kindled rats.

Cyclic enaminone esters,

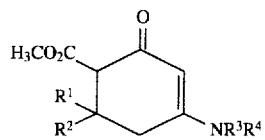

are synthesized from beta hydroxyketo esters,

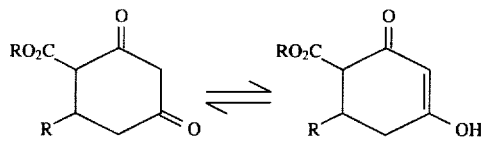

R = Alkyl which, in turn are synthesized by Michael addition of a vinyl ketone to a malonic ester, followed by a Claisen condensation (Method A), or by a base-catalyzed condensation of crotonate ester and acetoacetate (Method B) to form,

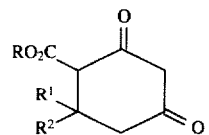

R=Alkyl; $R^1,R^2$=H, H; H, $CH_3$; $CH_3$, $CH_3$; $C_6H_5$, H.

Method B was preferred, especially in the case of 3-penten-2-one, which was available in only 65% purity. 5-Methylcyclohexane-1,3-dione was formed by the acid catalyzed decarboxylation of either methyl 6-methyl-2-oxo-cyclohex-3-en-1-oate or the ethyl ester.

The beta hydroxyketo esters are refluxed with one equivalent of the appropriate amino compound under various conditions to provide the desired product to produce enaminones

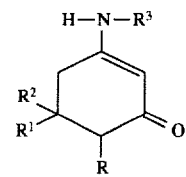

where,

3

R=H or an ester derivative;

R$^1$=H or CH$_3$;

R$^2$=H or CH$_3$; and

R$^3$=heterocyclic radicals, benzyls, hydrazinos, phenyls or substituted, disubstituted or trisubstituted derivatives thereof, wherein the substitution are from the group consisting of F, Cl, Br, I, C(CH$_3$)$_3$), CH$_3$, C$_2$H$_5$, OCH$_3$, NO$_2$, NH$_2$, CF$_3$ and OCF$_3$, In the case of the hydrazino radicals, a much lower temperature was employed, due, most probably to the lower pk$_a$ of the aniline (4.63 for aniline) derivatives compared to the benzylamine analogues (9.33 for benzylamine) (see, CRC Handbook of Chemistry and Physics, 65th Ed., R. C. Wease, Ed., CRC Press, Cleveland, Ohio (1985)) (Method D). The enaminone esters can, in turn, be reacted with additional amine to yield enaminone amides, either through the β-hydroxyketones (Method E) or through the intermediate enaminone esters (Method F).

DETAILED DESCRIPTION OF THE INVENTION

Melting points were determined on a Thomas Hoover capillary melting point apparatus and are uncorrected. Observed boiling points were also uncorrected. IR spectra were recorded on samples in Nujol, or as diluted chloroform solutions in matched sodium chloride cells or neat with a Perkin-Elmer 1330 spectro-photometer. $^1$H NMR spectra were recorded on a General Electric QE 300-MHz spectrometer in deuterated solvents using tetramethylsilane as an internal reference. Elemental analyses (C, H, N, and halogen) were performed by Schwarzkopf Microanalytical Laboratory, Woodside, N.Y. Where analyses are indicated only by the symbols of the elements analytical results for the elements were within 0.4% of the theoretical values. Experimental data for the enaminone compounds are provided in Table I. Ethyl 4-hydroxy-6-methyl-2-oxo-cyclohex-3-en-1-oate was prepared by Method B with comparable yields with Method A employed in the literature (T. A. Spencer, M. D. Newton, S. W. Baldwin, *J. Org. Chem.* (1964), Vol. 29, 787–789). 19 and 36 were prepared by Method D with comparable yields to those reported in the literature (K. Kotera, *Yakugaku Zasshi* (1960), Vol. 91, 1275–1278). Typical experiments illustrating the general procedures for the preparation of the enaminones and intermediates are described below.

Methyl 4-hydroxy-6-methyl-2-oxocyclohex-3-en-1-oate (26) [R=CH$_3$, R$^1$=R$^2$=CH$_3$]

Method A.

To a freshly prepared solution of sodium (23 g, 1 g-atom) in methanol (300 mL) was added dimethyl malonate (132 g, 1 mol) and the mixture stirred on an ice bath for 15 minutes after the addition. Mesityl oxide (100 g, 1 mol) was added and the mixture stirred at room temperature for an additional 30 minutes. After refluxing for 12 hours, the white precipitate which separated was dissolved in a minimum amount of cold water, the aqueous solution was acidified with hydrochloric acid (400 mL of a 2.5M solution) and extracted with dichloromethane (4×200 mL). The organic phase was dried (Na$_2$SO$_4$), evaporated and the residue crystallized from toluene to give the title compound. The methanolic filtrate was evaporated to dryness and the residue dissolved in cold water, acidified with hydrochloric acid and extracted with dichloromethane. The residue was recrystallized from tolu-

4 ene. Total yield: 122.3 g (62%); mp 99–101° C.; $^1$H NMR (CDCl$_3$) δ1.14 (6H, d, 2×CH$_3$), 2.20 (2H, AB system, diastereotropic CH$_2$), 3.14 (1H, s, CH of cyclohexene ring), 3.70 (3H, s, OCH$_3$), 5.41 (1H, s, =CH—), 9.35 (1H, br s, —OH). Anal. (C, H).

Method B.

To a freshly prepared solution of sodium (17.8 g, 0.77 g-atom) in methanol (220 mL) was added methyl acetoacetate (89.7 g, 0.77 mol) over thirty minutes and the mixture stirred on an ice bath for an additional fifteen minutes. Ethyl crotonate (100 mL, 96% 0.77 mol) was added dropwise and the mixture stirred at room temperature for an additional 30 minutes. After refluxing for 2 hours, the mixture was cooled and the precipitate treated as indicated in Method A. Yield: 57 g (40%) with identical constants as in Method A.

5-Methylcyclohexane-1,3-dione (26') (R=R$^1$=H; R$^2$=CH$_3$)

Ethyl 4-hydroxy-6-methyl-2-oxocyclohex-3-3n-1-oate prepared by Method B, 129 g (0.59 mol as the sodium enolate) was dissolved in 60 mL of water, 118 mL of a 5M sodium hydroxide solution added and the mixture refluxed for 1 hour. After cooling to room temperature, the mixture was acidified with 90 mL of 5M sulfuric acid and extracted with dichloromethane (2×100 mL). After washing with water, the organic layer was dried over magnesium sulfate, the solvent removed under reduced pressure and the residue distilled, bp 60° C. (0.3 mm), 33.5 g (44.9%), which crystallized on standing for one week. Recrystallized from toluene, mp 71°–72° C. (Found: C, 66.4%; H, 8.0%. C$_7$H$_{10}$O$_2$ requires C, 66.6%; H, 8.0%).

Methyl 4-[(4'-chloro-2-pyridinyl)amino]-6-methyl-2-oxo-cyclohex-3-3n-1-oate (116)

Method C.

To a solution of 26 (R=CH$_3$; R$^1$=CH$_3$; R$^2$=H) (5 g, 27 mmol) in 140 mL benzene was added 2-amino-5-chloropyridine (3.86 g, 30 mmol) and the mixture refluxed for 5 hours using a Dean-Stark water separator. During the reaction, 0.50 mL of water was collected. A light yellow precipitate formed on cooling to room temperature (1.5 g, mp 197°–200° C.). The filtrate was evaporated under reduced pressure to yield an orange residue which was recrystallized from toluene to yield a second crop (1.95 g, mp 197°–198° C.). Further recrystallization of both crops from toluene gave 116, in a total yield of 43% (3.45 g, mp 206°–208° C.); $^1$H NMR (DMSO-d$_6$) δ0.96 (3H, d, J=4.89 Hz, CH$_3$), 2.24–3.58 (4H, m, CH$_2$+2CH of cyclohexene ring), 3.61 (3H, s, OCH$_3$), 6.82 (1H, s, =CH—), 7.03–8.32 (3H, m, pyridine ring), 9.57 (1H, s, —NH). Anal. (C, H, N, Cl).

Ethyl 4-{[(4'-chloro-2'-benzoyl)phenyl]amino}-6-methyl-2-oxo-cyclohex-3-en-1-oate (133)

Method D.

Compound 26 (R=C$_2$H$_5$; R$^1$=CH$_3$; R$^2$=H) (1.98 g, 10 mmol) (2) was dissolved in absolute ethanol (150 mL) and 2-amino-5-chlorobenzophenone (2.6 g, 11 mmol) added and the mixture refluxed for 4 h. After evaporating the solution under reduced pressure, the residual red oil was triturated with ethyl acetate-petroleum ether (bp 37°–54° C.) and refrigerated until crystals were formed. The crystals were collected and recrystallized from ethyl acetate to yield 133 (1.0 g, 24%, mp 154°–156° C.); $^1$H NMR (CDCl$_3$) 1.24 (3H, d, J=7.36 Hz, CH$_3$), 1.25 (3H, t, J=6.25 Hz, CH$_3$), 1.63–3.54

(3H, m, CH$_2$+CH of cyclohexene ring), 4.19 (3H, m, CH$_2$ of ethyl group+CH of cyclohexene ring), 7.16–7.56 (7H, m, C$_6$H$_5$+NH+vinyl H), 7.68–8.03 (3H, m, C$_6$H$_3$ ring). Anal. (C, H, N, Cl).

3-[(p-Chlorophenyl)amino]-5-methyl-2-cyclohexen-1-one (146)

Method D.

5-methyl-1,3-cyclohexanedione (5 g, 98%, 38.8 mmole) was added to p-chloroaniline (5.5 g, 42.7 mmole) dissolved in a mixture of benzene (100 mL) and absolute ethanol (75 mL) and was refluxed for 4 hours. Evaporation of the solvents produced a yellow solid (2.43 g, 31%) which was recrystallized successively from toluene (mp 195°–196° C.) and a mixture of ethyl acetate: acetone: methanol (2:2:1) and provided an analytical sample (mp 198°–199.5° C.). Workup of the mother liquors produced additional 146 (5.80 g), providing an overall yield of 88%; $^1$H NMR (DMSO-d$_6$) δ1.02 (3H, d, J=6.29 Hz, CH$_3$), 1.84–2.54 (5H, m, cyclohexene ring), 5.32 (1H, s, =CH—), 7.16–7.48 (4H, m, C$_6$H$_4$), 8.91 (1H, s, —NH). Anal. (C, H, N, Cl).

3-(4'-Chlorophenyl)amino-2-cyclopentenone (151)

Method D.

Cyclopentane-1,3-dione (5 g, 51 mmol) and p-chloroaniline (7.15 g, 56 mmol) were dissolved in a mixture of 50 mL benzene and 75 mL absolute ethanol and the mixture refluxed for 4 hours. On cooling and following evaporation under reduced pressure, a solid residue formed. This residue was recrystallized from acetone-methanol-ethyl acetate providing a yield of 8.83 g (84%), mp 215°–216° C.; $^1$H NMR (DMSO-d$_6$) δ2.21–2.76 (4H, m, cyclopentene ring), 5.45 (1H, s, =C—), 7.21–7.43 (4H, m, C$_6$H$_4$), 9.69 (1H, s, —NH). Anal (C, H, N, Cl).

Kinetic Hydrolysis.

Compound 27 (5.9 mg), was dissolved in 95% ethanol and diluted to 50 mL with ethanol. This solution was 4.0×10$^{-5}$M. Phosphate buffer, pH 7.4 and water were used in this study. All experiments were performed in triplicate. A volume of the stock ethanol solution of 1 (0.2 mL), was diluted with the appropriate solvent to make 1 mL of solution. Each mixture was sealed in a Teflon capped reaction vial and incubated at 37° C. for the same time periods as indicated in the ip rat toxicity study (Tables X and X-A). After each time period, the vials were removed from the incubator and quenched at –80° C. until ready for analysis. Initial scan (t=0 h) indicated a λ max at 311 nm for 27. The potential hydrolysis products, methyl 4-hydroxy-6-methyl-2-oxocyclohex-3-en-1-oate had a λ max of 277 nm and p-chloroaniline had a λ max of 232 nm under the same conditins. After all samples were incubated, the UV spectra was taken from 190–500 nm using the respective solvent as a blank. The results were plotted in terms of absorbance v, time of incubation and the absorbance values. The average absorbance values for 27 in aqueous media was 0.929 (range 0.789–1.069), while in pH 7.4 buffer the average value was 1.112 (range 0.983–1.240). However, the wavelength did not change from 311 nm. Statistical analysis revealed that these individual differences were not significant (p <0.05).

Enzymatic Hydrolysis.

A solution of (4×10$^{-5}$M), prepared as indicated above, Tris buffer (0.01M, pH 8.0) and esterase (EC 3.1.1.1, 200 units per mg, 19 mg dissolved in Tris buffer and diluted to 10 mL) was employed. The above assay was repeated in 1176X triplicating 0.2 mL of stock solution, 1 mL buffer and 0.1 mL of enzyme solution and the incubation carried out at 37° C. for each time period (0.25, 0.5, 1, 2, 4, 8 and 24 h). The blank (time=0 h) contained 0.2 mL of stock solution and 1.1 mL buffer, but no enzyme. After each time period, the samples were quenched with 1 mL methylene chloride and frozen at –80° C. until ready for assay. In a preliminary experiment, 27 and 146, each 4×10$^{-5}$M in methylene chloride were analyzed by UV spectroscopy. The λ max for 27 were 301.5 and 226.7 nm, while the λ max for 146 were 301.5 and 229.4 nm. The latter wavelength differentiation was employed in the subsequent assay. Each sample was thawed, and the methylene chloride layer scanned in the UV region.

Table I sets forth 75 enaminones prepared according to the recipes set out above. Table II sets forth the analytical results for compounds prepared in Table I. For those compounds not shown on Table II, the analytical results obtained were within ±0.4% of the theoretical values.

TABLE I

Physical Properties of Enaminones[a]

| No. | R | R$^1$ | R$^2$ | R$^3$ | mp. °C. or bp, °C. (mm) | formula |
|---|---|---|---|---|---|---|
| 11 | CONCH$_2$C$_6$H$_5$ | C$_6$H$_5$ | H | CH$_2$C$_6$H$_5$ | 219–220[g] | C$_{27}$H$_{26}$N$_2$O$_2$ |
| 12 | CO$_2$CH$_3$ | CH$_3$ | H | CH$_2$C$_6$H$_5$ | 154–155[d] | C$_{16}$H$_{19}$NO$_3$ |
| 13 | CO$_2$CH$_3$ | CH$_3$ | CH$_3$ | CH$_2$C$_6$H$_5$ | 138–139[d] | C$_{17}$H$_{21}$NO$_3$ |
| 14 | CO$_2$CH$_3$ | CH$_3$ | CH$_3$ | (CH$_2$)$_2$C$_6$H$_5$ | 130–131[f] | C$_{18}$H$_{23}$NO$_3$ |
| 15 | CON(CH$_2$)$_2$C$_6$H$_5$ | CH$_3$ | H | (CH$_2$)$_2$C$_6$H$_5$ | 171–172[d] | C$_{24}$H$_{28}$N$_2$O$_2$ |
| 16 | CO$_2$CH$_3$ | CH$_3$ | H | CH$_2$C$_6$H$_4$ (p-Cl) | 173–174° g | C$_{16}$H$_{18}$NO$_3$Cl |
| 17 | CO$_2$CH$_3$ | CH$_3$ | H | CH$_2$C$_6$H$_4$ (p-CH$_3$) | 160–163[g] | C$_{17}$H$_{21}$NO$_3$ |
| 18 | CO$_2$CH$_3$ | CH$_3$ | H | CH$_2$C$_6$H$_4$ (p-CO$_2$H) | 231–235 d.[g] | C$_{17}$H$_{19}$NO$_5$ |
| 19 | H | CH$_3$ | CH$_3$ | CH$_2$C$_6$H$_5$ | 124–127[g] | C$_{15}$H$_{19}$NO |
| 20 | CO$_2$CH$_3$ | CH$_3$ | H | CH$_2$C$_6$H$_4$ (p-NO$_2$) | 174–176[i] | C$_{16}$H$_{18}$N$_2$O$_5$ |
| 21 | CO$_2$CH$_3$ | CH$_3$ | H | CH$_2$C$_6$H$_4$ (p-F) | 174–176[g] | C$_{17}$H$_{18}$NO$_3$F |
| 22 | CONHCH$_2$C$_6$H$_5$ | CH$_3$ | H | CH$_2$C$_6$H$_5$ | 192–193[g] | C$_{22}$H$_{24}$N$_2$O$_2$ |
| 23 | CONHC$_6$H$_5$ | CH$_3$ | H | C$_6$H$_5$ | 243–244[j] | C$_{20}$H$_{20}$N$_2$O$_2$ |
| 24 | CO$_2$CH$_3$ | CH$_3$ | H | C$_6$H$_5$ | 141–144[f] | C$_{15}$H$_{17}$NO$_3$ |
| 25 | CO$_2$CH$_3$ | CH$_3$ | H | NHC$_6$H$_5$ | 167–167.5[k] | C$_{15}$H$_{18}$N$_2$O$_3$ |
| 26 | CO$_2$CH$_3$ | CH$_3$ | H | C$_6$H$_4$ (p-C$_2$H$_5$) | 152–157[f] | C$_{17}$H$_{21}$NO$_3$ |
| 27 | CO$_2$CH$_3$ | CH$_3$ | H | C$_6$H$_4$ (p-Cl) | 178–180[f] | C$_{15}$H$_{16}$NO$_3$Cl |
| 28 | CO$_2$CH$_3$ | CH$_3$ | H | C$_6$H$_4$ (p-CH$_3$) | 144–146[f] | C$_{16}$H$_{19}$NO$_3$.H$_2$O |
| 29 | CO$_2$CH$_3$ | CH$_3$ | H | C$_6$H$_4$ (p-NO$_2$) | 186–187[f] | C$_{15}$H$_{16}$N$_2$O$_5$ |
| 30 | CO$_2$CH$_3$ | CH$_3$ | H | C$_6$H$_5$ (2'-OCH$_3$,-5'-CH$_3$) | 160.5–161.5[f] | C$_{17}$H$_{21}$NO$_4$ |
| 31 | CO$_2$CH$_3$ | CH$_3$ | H | C$_6$H$_5$ (2',5'-(OCH$_3$)$_2$) | 134–135[f] | C$_{17}$H$_{21}$NO$_5$ |

TABLE I-continued

Physical Properties of Enaminones[a]

| No. | R | R[1] | R[2] | R[3] | mp. °C. or bp, °C. (mm) | formula |
|---|---|---|---|---|---|---|
| 32 | $CO_2CH_3$ | $CH_3$ | H | $C_6H_4$ (p-COOH) | 222–226 d.[g] | $C_{16}H_{17}NO_5$ |
| 33 | $CO_2CH_3$ | $CH_3$ | H | $N(CH_2)_2O$ | 200–202[k] | $C_{13}H_{20}N_2O_4$ |
| 34 | $CO_2CH_3$ | $CH_3$ | H | $N(CH_2)_2O$ | 207–212[g] | $C_{13}H_{20}N_2O_4$ |
| 35 | $CO_2CH_3$ | $CH_3$ | H | $C_6H_4$ (p-OH) | 182–183[f] | $C_{15}H_{17}NO_5$ |
| 36 | H | $CH_3$ | $CH_3$ | $C_6H_5$ | 181–183[f] | $C_{14}H_{17}NO$ |
| 108 | $CO_2CH_3$ | $CH_3$ | H | $CH(CH_3)C_6H_5$ | 190–193[k] | $C_{17}H_{21}NO_3$ |
| 109 | $CO_2CH_3$ | $CH_3$ | H | $(CH_2)_2C_6H_5$ | 116–118[k] | $C_{17}H_{21}NO_3$ |
| 110 | $CO_2CH_3$ | $CH_3$ | H | $(CH_2)_3C_6H_5$ | 163–164[l] | $C_{18}H_{23}NO_3$ |
| 111 | $CO_2CH_3$ | $CH_3$ | H | $(CH_2)_4C_6H_5$ | 90–92[m] | $C_{19}H_{25}NO_3$ |
| 112 | $CO_2CH_3$ | $CH_3$ | H | $C_6H_4$ (p-F) | 161–164[n] | $C_{15}H_{16}NO_3F$ |
| 113 | $CO_2CH_3$ | $CH_3$ | H | $C_6H_4$ (p-Br) | 188–190[o] | $C_{15}H_{16}NO_3Br$ |
| 114 | $CO_2CH_3$ | $CH_3$ | H | $C_6H_4$(p-C(CH_3)_3) | 221–222[n] | $C_{19}H_{25}NO_3$ |
| 115 | $CH_2CH_3$ | $CH_3$ | H | $C_6H_4$ (p-CF_3) | 169–170[m] | $C_{16}H_{16}NO_3F_3$ |
| 116 | $CO_2CH_3$ | $CH_3$ | H | 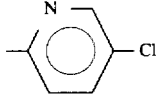 | 206–208[k] | $C_{14}H_{15}N_2O_3$ |
| 117 | $CO_2CH_3$ | $CH_3$ | $CH_3$ | $C_6H_5$ | 168–169[d] | $C_{16}H_{19}NO_3$ |
| 118 | $CO_2CH_3$ | $CH_3$ | $CH_3$ | $C_6H_4$ (p-NO_2) | 178–179[m] | $C_{16}H_{18}N_2O_5$ |
| 119 | $CO_2CH_3$ | $CH_3$ | $CH_3$ | $C_6H_4$ (p-Cl) | 141–143[d] | $C_{16}H_{18}NO_3Cl$ |
| 120 | $CO_2CH_3$ | $CH_3$ | $CH_3$ | $C_6H_4$ (p-C(CH_3)_3) | 170–171[m] | $C_{20}H_{27}NO_3$ |
| 121 | $CO_2CH_3$ | $CH_3$ | $CH_3$ | $C_6H_4$ (p-CF_3) | 158–159[m] | $C_{17}H_{18}NO_3F_3$ |
| 122 | $CO_2C_2H_5$ | $CH_3$ | H | $C_6H_4$ (p-Cl) | 161–163[d] | $C_{16}H_{18}NO_3Cl$ |
| 123 | $CO_2C_2H_5$ | $CH_3$ | H | $C_6H_4$ (p-Br) | 151–154[d] | $C_{16}H_{18}NO_3Br$ |
| 124 | $CO_2C_2H_5$ | $CH_3$ | H | $C_6H_4$ (p-F) | 150–151.5[d] | $C_{16}H_{18}NO_3F$ |
| 125 | $CO_2C_2H_5$ | $CH_3$ | H | $C_6H_4$ (p-CH_3) | 134.5–135.5[m] | $C_{17}H_{21}NO_3$ |
| 126 | $CO_2C_2H_5$ | $CH_3$ | H | $C_6H_4$ (p-C_2H_5) | 148.5–150[m] | $C_{18}H_{23}NO_3$ |
| 127 | $CO_2C_2H_5$ | $CH_3$ | H | $C_6H_4$ (p-NO_2) | 173–175[d] | $C_{16}H_{18}N_2O_5$ |
| 128 | $CO_2C_2H_5$ | $CH_3$ | H | $C_6H_5$ (2',5'-(OCH_3)_2) | 137–138[d] | $C_{18}H_{23}NO_5$ |
| 129 | $CO_2C_2H_5$ | $CH_3$ | H | $C_6H_5$ | 155–158[n] | $C_{16}H_{19}NO_3$ |
| 130 | $CO_2C_2H_5$ | $CH_3$ | H | $C_6H_4$ (p-C(CH_3)_3) | 165.5–166[d] | $C_{20}H_{27}NO_3$ |
| 131 | $CO_2C_2H_5$ | $CH_3$ | H | $C_6H_4$ (p-CF_3) | 184.5–186[d] | $C_{17}H_{18}NO_3F_3$ |
| 132 | $CO_2C_2H_5$ | $CH_3$ | H | $CH_2C_6H_5$ | 134.5–135.5[m] | $C_{17}H_{21}NO_3$ |
| 133 | $CO_2C_2H_5$ | $CH_3$ | H |  | 153–154.5[m] | $C_{23}H_{22}NO_4Cl$ |
| 134 | $CONHCH_2C_6H_4$ (p-F) | $CH_3$ | H | $CH_2C_6H_4$ (p-F) | 183–184[p] | $C_{22}H_{22}N_2O_2F$ |
| 137 | H | $CH_3$ | $CH_3$ | $C_6H_4$ (p-Cl) | 208–210[p] | $C_{14}H_{16}NOCl$ |
| 138 | H | $CH_3$ | $CH_3$ | $C_6H_4$ (p-NO_2) | 242–244[p] | $C_{14}H_{16}N_2O_3$ |
| 139 | H | $CH_3$ | $CH_3$ | $C_6H_4$ (p-CH_3) | 203–204[q] | $C_{15}H_{19}NO$ |
| 140 | H | $CH_3$ | $CH_3$ | $C_6H_4$ (p-C_2H_5) | 201–202.5[q] | $C_{16}H_{21}NO$ |
| 141 | H | $CH_3$ | $CH_3$ | $C_6H_4$ (p-OCH_3) | 189–191[d] | $C_{15}H_{19}NO_2$ |
| 142 | H | $CH_3$ | $CH_3$ | $C_6H_4$ (p-NH_2) | 211.5–212.5[q] | $C_{14}H_{18}N_2O$ |
| 143 | H | $CH_3$ | $CH_3$ | $C_6H_4$ (p-C(CH_3)_3) | 206–208[n] | $C_{18}H_{25}NO$ |
| 144 | H | $CH_3$ | $CH_3$ | $C_6H_4$ (p-CF_3) | 240.5–241.5[n] | $C_{15}H_{16}NOF_3$ |
| 145 | H | $CH_3$ | $CH_3$ | $(CH_2)_2C_6H_5$ | 121–123[d] | $C_{16}H_{21}NO$ |
| 146 | H | $CH_3$ | H | $C_6H_4$ (p-Cl) | 198–199.5[?] | $C_{13}H_{14}NOCl$ |
| 147 | H | H | H | $C_6H_4$ (p-Cl) | 190–191.5[i] | $C_{12}H_{12}NOCl$ |
| 148 | H | H | H | $CH_2C_6H_5$ | 125–127[s] | $C_{13}H_{15}NO$ |
| 149 | H | H | H | $(CH_2)_2C_6H_5$ | 93.5–95[o] | $C_{14}H_{17}NO$ |
| 150 | H | H | H | $C_6H_4$ (p-C(CH_3)_3) | 185–187[n] | $C_{16}H_{21}NO$ |
| 151 | H | H | H | $C_6H_4$ (p-CF_3) | 203–204[d] | $C_{13}H_{12}NOF_3$ |
| 152 | H | H | H | $C_6H_4$ (p-Cl) | 216–217[r] | $C_{12}H_{11}NOCl$ |
| 153 | H | H | H | $CH_2C_6H_5$ | 139–141.5[g] | $C_{13}H_{15}NO$ |
| 154 | H | H | H | $(CH_2)_2C_6H_5$ | 136–138[?] | $C_{14}H_{17}NO$ |

[a]The infrared and $^1$H NMR spectra were consistent with assigned structures.
[b]Recrystallization solvents as indicated.
[c]EtOAc-petroleum ether (80°100° C.).
[d]EtOAc.
[e]EtOAc-ligroine (70–90° C.).
[f]2-Propanol.
[g]Methanol.
[i]Methanol-$H_2O$.
[j]Toluene-methanol.

TABLE I-continued

Physical Properties of Enaminones[a]

| No. | R | R[1] | R[2] | R[3] | mp. °C. or bp, °C. (mm) | formula |
|---|---|---|---|---|---|---|

[k]Toluene.
[l]EtOAc/EtOH.
[m]EtOAc/Petroleum ether (bp 38–54° C.).
[n]EtOAc/Me$_2$CO.
[o]2-PrOH/Me$_2$CO.
[p]MeOH/Me$_2$CO.
[q]EtOH.
[r]EtOAc:MeOH (2:2:1).
[s]2-PrOH.

TABLE II

Analyses of Enaminones

| Compd. | Empirical Form | Elements Analyzed | Calculated | Found |
|---|---|---|---|---|
| 5 | $C_{14}H_{21}NO_3$ | C, H, N | 66.93, 8.36, 5.58 | 66.82, 8.29, 5.51 |
| 6 | $C_{14}H_{21}NO_4$ | C, H, N | 62.92, 7.87, 4.87 | 62.79, 7.76, 5.42 |
| 7 | $C_{13}H_{19}NO_4$ | C, H, N | 61.66, 7.51, 5.53 | 61.62, 7.45, 5.41 |
| 8 | $C_{18}H_{21}NO_4$ | C, H, N | 68.57, 6.67, 4.44 | 68.70, 6.85, 4.40 |
| 9 | $C_{13}H_{19}NO_3$ | C, H, N | 65.82, 8.02, 5.91 | 65.65, 8.20, 5.90 |
| 10 | $C_{19}H_{23}NO_3$ | C, H, N | 72.84, 7.35, 4.47 | 72.80, 7.50, 4.50 |
| 11 | $C_{27}H_{26}N_2O_2$ | C, H, N | 79.02, 6.34, 6.83 | 78.83, 6.44, 6.74 |
| 12 | $C_{16}H_{19}NO_3$ | C, H, N | 70.33, 6.96, 5.13 | 70.60, 7.10, 5.10 |
| 13 | $C_{17}H_{21}NO_3$ | C, H, N | 71.08, 7.32, 4.87 | 71.34, 7.26, 4.95 |
| 14 | $C_{18}H_{23}NO_3$ | C, H, N | 71.76, 7.64, 4.65 | 71.87, 7.71, 4.61 |
| 15 | $C_{24}H_{28}N_2O_2$ | C, H, N | 76.60, 7.45, 7.45 | 76.50, 7.60, 7.50 |
| 16 | $C_{16}H_{18}NO_3Cl$ | C, H, N, Cl | 62.49, 5.91, 4.55, 11.52 | 62.32, 5.91, 4.50, 11.36 |
| 17 | $C_{17}H_{21}NO_3$ | C, H, N | 71.04, 7.38, 7.84 | 70.83, 7.34, 4.76 |
| 18 | $C_{17}H_{19}NO_5$ | C, H, N | 64.33, 6.05, 4.41 | 64.60, 6.02, 4.44 |
| 19 | $C_{15}H_{19}NO$ | C, H, N | 78.55, 8.37, 6.11 | 78.38, 8.23, 5.99 |
| 20 | $C_{16}H_{18}N2O_5$ | C, H, N | 60.36, 5.71, 8.80 | 60.56, 5.66, 8.71 |
| 21 | $C_{16}H_{17}NO_3F$ | C, H, N, F | 66.18, 5.91, 4.83, 6.54 | 65.94, 6.03, 4.75, 6.80 |
| 22 | $C_{22}H_{24}N_2O_2$ | C, H, N | 75.82, 6.96, 8.04 | 75.67, 7.00, 8.11 |
| 23 | $C_{20}H_{20}N2O_2$ | C, H, N | 74.96, 6.30, 8.74 | 75.06, 6.25, 8.60 |
| 24 | $C_{15}H_{17}NO_3$ | C, H, N | 69.47, 6.62, 5.40 | 69.25, 6.40, 5.27 |
| 25 | $C_{15}H_{18}N2O_3$ | C, H, N | 65.66, 6.63, 10.21 | 65.82, 6.74, 10.45 |
| 26 | $C_{17}H_{21}NO_3$ | C, H, N | 71.04, 7.38, 4.87 | 70.83, 7.14, 4.85 |
| 27 | $C_{15}H_{16}NO_3Cl$ | C, H, N, Cl | 61.32, 5.50, 4.77, 12.07 | 61.05, 5.42, 4.81, 11.82 |
| 28 | $C_{16}H_{19}NO_3 \cdot H_2O$ | C, H, N | 65.95, 6.59, 4.80 | 66.04, 6.55, 4.84 |
| 29 | $C_{15}H_{16}N_2O_5$ | C, H, N | 59.20, 5.31, 9.21 | 59.00, 5.12, 8.95 |
| 30 | $C_{17}H_{21}NO_4$ | C, H, N | 67.30, 6.99, 4.62 | 67.15, 6.89, 4.53 |
| 31 | $C_{17}H_{21}NO_5$ | C, H, N | 63.92, 6.64, 4.39 | 64.02, 6.89, 4.25 |
| 32 | $C_{16}H_{17}NO_5$ | C, H, N | 63.35, 5.66, 4.62 | 63.18, 5.43, 4.79 |
| 33 | $C_{13}H_{20}N_2O_4$ | C, H, N | 58.18, 7.53, 10.44 | 58.23, 7.35, 10.17 |
| 34 | $C_{13}H_{20}N2O_4$ | C, H, N | 58.18, 7.53, 10.44 | 58.14, 7.65, 10.49 |
| 35 | $C_{15}H_{17}NO_3$ | C, H, N | 65.43, 6.24, 5.09 | 65.37, 6.32, 5.06 |
| 36 | $C_{14}H_{17}NO$ | C, H, N | 78.08, 7.97, 6.51 | 77.73, 7.66, 6.37 |

NMR results at 300 MHz of the enaminones were consistent with the assigned structures. Of particular interest was the assignment of the methoxy groups in methyl 4-(2', 5'-dimethoxy)-phenylamino-6-methyl-2-oxo-cyclohex-3-en-1-oate, 31. The chemical shifts (δ ppm) for the carbomethoxy, 2'-methoxy, and 5'-methoxy protons occurred at 3.81, 3.84 and 3.78, respectively.

To determine whether the condensation of cyclic 1,3-dicarbonyl analogs with benzylamine, substituted benzylamines, aniline, substituted anilines and hydrazines produced stable, water-soluble, highly potent and non-toxic compounds possessing anticonvulsant activity comparable to those agents currently commercially available, compounds produced as described were assayed for anticonvulsant activity by the Antiepileptic Drug Development (ADD) Program, Epilepsy Branch, Neurological Disorders Program, National Institute of Neurological and Communicative Disorders and Stroke, National Institutes of Health.

The first phase of the ADD Program involved performing tests on male Carworth Farms #1 mice. Each novel enaminone compound was tested at least 3 dose levels (30, 100, 300 mg/kg) as described (Anticonvulsant Screening Project, Antiepileptic Drug Development Program, National Institutes of Health, DHEW Publ. (NIH) (U.S.) (1978), NIH 78-1093; R. J. Porter, J. J. Cereghino, G. D. Gladding, B. J. Hessie, H. J. Kupferberg, B. Scoville, B. G. White, Cleveland Clin. Q. (1984), vol. 51, 293–301; R. L. Krall, J. K. Penry, B. G. White, H. J. Kupferberg, E. A. Swinyard, Epilepsia (1978), Vol. 19, 400–422). The vehicle used to solubilize each compound, the tests undertaken and related data are indicated on the test results form found in the subsequent pages of this application. Three tests were performed:

1. MES—Electroshock Seizure Test

Maximal electroshock seizures are elicited with a 60-cycle alternating current of 50 mA intensity (5–7 times that necessary to elicit minimal electroshock seizures) delivered via corneal electrodes for 0.2 seconds. A drop of 0.9% saline is instilled in the eye prior to application of the electrodes in order to prevent the death of the animal. Abolition of the hind limb tonic extension component of the seizure is defined as protection and results are expressed as the number of animals protected/the number of animals tested.

2. sc Met—Subcutaneous Pentylenetetrazol (Metrazol$^R$) Seizure Test

Eighty-five mg/kg of pentylenetetrazol, which induces seizures in more than 95% of mice) is administered as a 0.5% solution subcutaneously in the posterior midline. The animal is observed for 30 minutes. Failure to observe even a threshold seizure (a single episode of clonic spasms of at least 5 seconds duration) is defined as protection and the results are expressed as the number of animals protected/the number of animals tested.

3. Tox—Toxicity

The rotorod test is used to elevate neurotoxicity. The animal is placed on a 1 inch diameter knurled plastic rod rotating at 6 rpm. Normal mice can remain on a rod rotating at this speed indefinitely. Neurologic toxicity is defined as the failure of the animal to remain on the rod for 1 minute and the results are expressed as the number of animals protected/the number of animals tested.

TABLE III

Anticonvulsant Screening Project (ASP): Phase I Test Results

| Compound | Dose mg/kg | MES$^a$ 30 min | MES$^a$ 4 h | scMet$^b$ 30 min | scMet$^b$ 4 h | Tox$^c$ 30 min | Tox$^c$ 4 h |
|---|---|---|---|---|---|---|---|
| 12 | 10 | 2/3 | 0/3 | 0.1 | 0.1 | 0.8 | 0.4 |
|  | 300 | 1/1$^e$ | 0/1$^d$ | 0/1 | 0/1$^d$ | 3/4 | 0/2 |
| 13 | 300 | 1/1 | 0/1 | 0/1 | 0/1$^d$ | 1/4 | 0/2 |
| 14 | 100 | 1/3 | 0/3 | 0/1 | 0/1 | 0/8 | 0/4 |
|  | 300 | 1/1 | 0/1$^d$ | 0/1 | 0/1 | 1/4 | 0/2 |
| 15 | 300 | 0/1 | 1/1 | 0/1 | 0/1 | 0/4 | 0/2 |
| 16 | 300 | 1/1 | 1/1 | 1/1 (0/4) | 0/1 | 0/4 (0/4) | 0/2 |
| 19 | 100 | 1/3 | 0/3 | 0/1 | 0/1 | 0/8 | 0/4 |
|  | 300 | 1/1 | 1/1$^d$ | 0/1 | 0/1 | 1/4 | 0/2 |
| 21 | 300 | 0/1 | 1/1 | 0/1 | 0/1 | 0/4 | 0/2 |
| 25 | 300 | 1/1 | 0/1 | 1/1 (0/4) | 0/1 | 0/4 (0/4) | 0/2 |
| 26 | 100 | 2/3 | 0/3 | 0/1 | 0/1 | 0/8 | 0/4 |
| 27 | 100 | 3/3 | 0/3 | 0/1 | 0/1 | 1/8 | 0/4 |
|  | 300 | 1/1 | 1/1 | 0/1 | 0/1 | 4/4 | 0/2 |
| 28 | 30 | 0/1 | 0/1 | 1/1 (0/4) | 0/1 | 0/4 (0/4) | 0/2 |
|  | 300 | 1/1$^d$ | 0/1$^d$ | 0/1 | 0/1 | 2/4 | 0/2 |
| 29 | 100 | 0/3 | 0/3 | 1/1 (0/4) | 0/1 | 0/8 (0/4) | 0/4 |
| 31 | 100 | 1/3 | 0/3 | 0/1 | 0/1 | 0/8 | 0/4 |
|  | 300 | 1/1 | 0/1 | 0/1 | 0/1 | 0/4 | 0/2 |
| 36 | 100 | 2/3 | 0/3 | 0/1 | 0/1 | 0/8 | 0/4 |
|  | 300 | 1/1 | 0/1 | 0/1 | 0/1 | 0/4 | 0/2 |
| 109 | 100 | 2/3 | 0/3 | 0/1 | 0/1 | 0/8 | 0/4 |
|  | 300$^e$ | 1/1 | 0/1 | 0/1 | 0/1 | 4/4 | 2/2 |
| 112 | 100 | 2/3 | 0/3 | 0/1 | 0/1 | 0/8 | 0/4 |
|  | 300$^e$ | 1/1 | 1/1 | 0/1 | 0/1 | 4/4 | 0/2 |
| 113 | 100 | 3/3 | 3/3 | 0/1 | 0/1 | 0/8 | 0/4 |
|  | 300$^e$ | 1/1 | 1/1 | 2/5 | 0/1 | 0/4 | 0/2 |
| 115 | 100 | 3/3 | 1/3 | 0/1 | 0/1 | 0/8 | 0/4 |
|  | 300$^e$ | 1/1 | 1/1 | 2/5 | 0/1 | 0/4 | 0/2 |
| 116 | 100 | 2/3 | 0/3 | 0/1 | 0/1 | 0/8 | 0/4 |
|  | 300$^e$ | 1/1 | 0/1$^f$ | 1/1 (3/4) | 0/1 | 1/4 (0/4) | 0/2 |
| 118 | 300$^g$ | 0/1 | 1/1 | 0/1 | 0/1 | 0/4 | 0/2 |
| 119 | 100 | 3/3 | 3/3 | 0/1 | 0/1 | 8/8 | 2/4 |

TABLE III-continued

Anticonvulsant Screening Project (ASP): Phase I Test Results

| Compound | Dose mg/kg | MES$^a$ 30 min | MES$^a$ 4 h | scMet$^b$ 30 min | scMet$^b$ 4 h | Tox$^c$ 30 min | Tox$^c$ 4 h |
|---|---|---|---|---|---|---|---|
|  | 300$^e$ | 1/1 | 1/1 | 1/1 | 1/1 | 4/4$^h$ | 2/2 |
| 121 | 100 | 3/3 | 3/3 | 0/1 | 0/1 | 2/8 | 4/4 |
|  | 300 | 1/1 | 1/1 | 0/1 | 0/1 | 4/4 | 2/2 |
| 122 | 100 | 3/3 | 0/3 | 0/1 | 0/1 | 0/8 | 0/4 |
|  | 300$^e$ | 1/1 | 1/1 | 1/1 (2/4) | 0/1 | 4/4 (4/4) | 0/2 |
| 123 | 100 | 3/3 | 2/3 | 0/1 | 0/1 | 0/8 | 0/4 |
|  | 300$^e$ | 1/1 | 1/1 | 0/1 | 0/1 | 0/4 | 0/2 |
| 124 | 100 | 3/3 | 0/3 | 0/1 | 0/1 | 1/8 | 0/4 |
|  | 300 | 1/1 | 0/1 | 1/1 (2/4) | 0/1 | 4/4 | 0/2 |
| 125 | 100 | 1/3 | 0/3 | 0/1 | 0/1 | 0/8 | 0/4 |
|  | 300$^e$ | 1/1 | 0/1 | 0/1 | 0/1 | 0/4 | 0/2 |
| 126 | 300$^e$ | 1/1 | 0/1 | 0/1 | 0/1 | 0/4 | 0/2 |
| 127 | 100 | 3/3 | 0/3 | 0/1 | 0/1 | 0/8 | 0/4 |
|  | 300$^e$ | 1/1 | 0/1 | 1/1 (2/4) | 0/1 | 4/4 (4/4) | 0/2 |
| 128 | 300$^e$ | 1/1 | 0/1 | 0/1 | 0/1 | 0/4 | 0/2 |
| 130 | 100 | 1/3 | 0/3 | 0/1 | 0/1 | 0/8 | 0/4 |
|  | 300$^e$ | 1/1 | 0/1 | 0/1 | 0/1 | 0/4 | 0/2 |
| 131 | 100 | 3/3 | 0/3 | 0/1 | 0/1 | 0/8 | 0/4 |
|  | 300$^e$ | 1/1 | 1/1 | 0/1 | 0/1 | 0/4 | 0/2 |
| 138 | 100 | 1/3 | 0/3 | 0/1 | 0/1 | 0/8 | 0/4 |
|  | 300$^e$ | 1/1 | 0/1 | 0/1 | 0/1 | 0/4 | 0/2 |
| 140 | 300$^g$ | 0/1 | 1/1 | 0/1 | 0/1 | 0/4 | 0/2 |
| 142 | 100 | 0/3 | 1/3 | 0/1 | 0/1 | 0/8 | 0/4 |
|  | 300$^e$ | 1/1 | 1/1 | 0/1 | 0/1 | 0/4 | 0/2 |
| 143 | 100 | 0/3 | 0/3 | 1/5 | 0/1 | 0/8 | 0/4 |
|  | 300 | 0/1 | 0/1 | 1/5 | 0/1 | 0/4 | 0/2 |
| 144 | 100 | 0/3 | 2/3 | 0/1 | 0/1 | 0/8 | 0/4 |
|  | 300 | 0/1 | 0/1 | 1/1 | 0/1 | 0/4 | 0/2 |
| 145 | 300$^e$ | 1/1 | 0/1 | 0/1$^i$ | 0/1 | 4/4 | 0/2 |
| 146 | 100 | 3/3 | 0/3 | 0/1 | 0/1 | 0/8 | 0/4 |
|  | 300 | 1/1$^f$ | 1/1$^f$ | 2/5 | 0/1 | 2/4 | 2/2 |
| 147 | 100 | 3/3 | 0/3 | 0/1 | 0/1 | 8/8 | 0/4 |
|  | 300$^e$ | 1/1 | 1/1 | 0/1 | 0/1 | 4/4$^h$ | 1/2 |
| 148 | 100 | 3/3 | 0/3 | 0/1 | 0/1 | 0/8 | 0/4 |
|  | 300 | 1/1 | 0/1 | 0/1 | 0/1 | 4/4$^j$ | 0/2 |
| 149 | 100 | 3/3 | 0/3 | 0/1 | 0/1 | 4/8 | 0/4 |
|  | 300 | 1/1 | 0/1 | 0/0$^k$ | 0/1 | 4/4$^h$ | 1/2$^l$ |
| 150 | 100 | 3/3 | 0/3 | 0/1 | 0/1 | 0/8 | 0/4 |
|  | 300 | 1/1 | 1/1 | 3/5 | 0/1 | 4/4 | 0/2 |
| 151 | 100 | 3/3 | 0/3 | 0/1 | 0/1 | 0/8 | 0/4 |
|  | 300 | 1/1 | 1/1 | 0/1 | 0/1 | 4/4 | 0/2 |
| 152 | 100 | 1/3 | 0/3 | 0/1 | 0/1 | 0/8 | 0/4 |
|  | 300 | 1/1 | 0/1 | 0/1 | 0/1 | 0/4 | 0/2 |
| 153 | 100 | 3/3 | 0/3 | 0/1 | 0/1 | 0/8 | 0/4 |
|  | 300 | 1/1 | 1/1 | 0/1 | 0/1 | 4/4$^j$ | 0/2 |
| 154 | 300 | 1/1 | 0/1 | 0/1 | 0/1 | 4/4$^j$ | 0/2 |

$^a$Maximal electroshock test (number of animals protected/number of animals tested).
$^b$Subcutaneous pentylenetetrazol test.
$^c$Toxicity (number of animals exhibiting toxicity/number of animals tested). Results in parentheses are the results of a second trial.
$^d$Toxic at 30 min. Other compounds in Table I were inactive at doses up to 300 mg/kg.
$^e$0/2 MES animals dead after 24 h at 300 mg/kg.
$^f$Toxic at 30 min.
$^g$0/1 MES animals dead after 24 h at 300 mg/kg.
$^h$Unable to hold onto retorod.
$^i$Continuous seizure activity followed by death.
$^j$Unable to grasp rotorod.
$^k$Died during test without having seizure.
$^l$Toxic at 4 h.
$^m$One uanble to grasp rotorod.
$^n$Exhibited sweating and hyperactivity.
$^o$Died.

TABLE IV

Anticonvulsant Screening Project (ASP): Phase I Test Results

| COMPOUND | ASP Classification[d] |
|---|---|
| 12 | 1 |
| 13 | 2 |
| 14 | 1 |
| 15 | 2 |
| 16 | 2 |
| 19 | 1 |
| 21 | 2 |
| 25 | 2 |
| 26 | 1 |
| 27 | 1 |
| 28 | 1 |
| 29 | 1 |
| 31 | 1 |
| 36 | 1 |
| 109 | 1 |
| 112 | 1 |
| 113 | 1 |
| 115 | 1 |
| 116 | 1 |
| 118 | 2 |
| 119 | 1 |
| 121 | 1 |
| 122 | 1 |
| 123 | 1 |
| 124 | 1 |
| 125 | 1 |
| 126 | 2 |
| 127 | 1 |
| 128 | 2 |
| 130 | 1 |
| 131 | 1 |
| 138 | 1 |
| 140 | 2 |
| 142 | 1 |
| 143 | 1 |
| 144 | 1 |
| 145 | 2 |
| 146 | 1 |
| 147 | 1 |
| 148 | 1 |
| 149 | 1 |
| 150 | 1 |
| 151 | 1 |
| 152 | 1 |
| 153 | 1 |
| 154 | 2 |

[a]The classifications are as follows: 1, anticonvulsant activity at 100 mg/kg or less; 2, anticonvulsant activity at doses greater than 100 mg/kg.

The results of the Phase I tests for those compounds which displayed anticonvulsant activity are presented on Table III. Table IV presents the results of the Phase I tests in which the compounds are classified according to their anticonvulsant activity. Because compounds 16, 25 and 28 gave spurious results in the scMet evaluation, testing of these compounds was halted.

As a result of these tests, compounds 12, 13, 27, 31 and 36 were advanced to the Phase II testing regimen. In the second phase of the ADD program protocol, estimates of anticonvulsant activity and neurotoxicity are quantified. The median effective dose (ED50) in the MES, sc Met, and rotorod test is determined. In the case of a compound with apparent activity in only one anticonvulsant test, testing is carried out in the other up to, and in some cases beyond, doses which produce neurological deficit. Compounds which fail to produce minimal neurological deficit are tested whenever possible to doses ten times their lowest anticonvulsant ED50. Determination of the MES and sc Met ED50 is carried out at the time of peak effect in the tests, except when preliminary testing indicates that activity occurs at another time. The rotorod ED50 is determined at the time of the peak neurologic deficit.

The results of the Phase II tests are shown in Table V. Also included is data for several currently marketed anticonvulsants for comparison. The protective indices for 12 (7.73) and 27 (9.72) compare favorably with phenytoin (9.59) and both far surpass valproate (1.90). It should also be noted that the criteria for the evaluation of toxicity for the three commercial compounds is not the same as for the compounds synthesized herein. Whereas compounds 12, 13, 27 and 36 were evaluated for the ability of the test animals to remain on the rotorod, the commercial products were based on the onset of ataxia. It should be noted that none of the compounds reported displayed ataxia.

TABLE V

Phase II Quantification Data

| Compound | MES, ED50[a,b] | TD50[a,c] | PI, MES[d] | TPE[e] activity | TPE[e] toxicity |
|---|---|---|---|---|---|
| 12 | 64.70 (41.41–88.86) | >500 (nd) | 7.73 | 0.5 | 1 |
| 13 | 131.90 (92.33–188.5) | >500 (nd) | 3.79 | 0.5 | 1 |
| 27 | 26.20 (16.57–40.36) | 254.78 (202.15–321.81) | 9.72 | 0.5 | 2 |
| 36 | 109.38 (87.91–124.31) | 232.58 (199.94–273.09) | 2.13 | 0.5 | 0.5 |
| phenytoin | 9.04 (7.39–10.6) | 86.7 (80.4–96.1) | 9.59 | 2 | 2 |
| carbamazepine | 15.4 | 217 | 14.1 | 0.5 | 0.5 |

TABLE V-continued

Phase II Quantification Data

| Compound | MES, ED50[a,b] | TD50[a,c] | PI, MES[d] | TPE[e] activity | TPE[e] toxicity |
|---|---|---|---|---|---|
| valproate | (12.4–17.3) 665 (605–728) | (131–270) 1264 (800–2250) | 1.90 | 1 | 2 |

[a]ED50 and TD50 values are in milligrams/kilogram of test drug delivered intraperitoneally (ip).
[b]Measured at time of peak effect.
[c]Measured at time of peak neurologic deficit.
[d]PI = protective index (TD50/ED50).
[e]Time of peak effect.
Numbers in parentheses are 95% confidence interval.
nd = not determined.

TABLE V-A

Additional Phase II Data

| Compound | Dose, mg/kg | Time h, | MES[a] | Tox[b] |
|---|---|---|---|---|
| 118 | 100 | 2.00 | 0/2 | 0/2 |
|  |  | 3.00 | 0/2 | 0/2 |
| 121 | 3 | 0.50 | 0/4 | 0/4 |
|  | 10 | 0.50 | 0/4 | 0/4 |
| 122 | 3 | 0.50 | 0/4 | 0/4 |
|  | 10 | 0.50 | 1/4 | 0/4 |
| 126 | 100 | 0.25 | 2/2 | 0/2 |
|  |  | 1.00 | 0/2 | 0/2 |
| 127 | 3 | 0.50 | 0/4 | 0/4 |
|  | 10 | 0.50 | 0/4 | 0/4 |
| 128 | 100 | 0.25 | 0/2 | 0/2 |
|  |  | 1.00 | 0/2 | 0/2 |
| 140 | 100 | 2.00 | 0/2 | 0/2 |
|  |  | 3.00 | 0/2 | 0/2 |
| 142 | 100 | 0.25 | 1/2 | 0/2 |
|  |  | 1.00 | 1/2 | 0/2 |
| 145 | 100 | 0.25 | 0/2 | 0/2 |
|  |  | 1.00 | 0/2 | 0/2 |
| 154 | 100 | 0.25 | 2/2 | 0/2 |
|  |  | 1.00 | 0/2 | 0/2 |

[a]Maximal electroshock test (refer to Table III for definition).
[b]Rotorod toxicity (refer to Table III for definition).
[c]Inactive in scMet evaluations during the same time periods.

Due to the need for more rapid evaluation of the enaminones, a special intraperitoneal (ip) time of peak effect and toxicity evaluation was performed in mice on 116, 122, 123, 125, 130 and 131, which showed anti-MES protecting ability in phase I. These results are shown in Table VI. Table VII shows MES activity evaluated at 10 mg/kg and toxicity monitored at 100 mg/kg compounds 113 and 115, which were subsequently evaluated at the same dosage in rats. The ip ED 50 and TD 50 for 113 and 115 are shown in Table VIII.

TABLE VI

Intraperitoneal (ip) time of peak effect and toxicity of Compounds 116, 122, 123, 125, 130 and 131.

| Compound | Time, h | MES[a] 10 mg/kg | Tox[a] 100 mg/kg |
|---|---|---|---|
| 116 | 0.25 | 3/4 | 1/8[b] |
|  | 0.50 | 4/4 | 6/8[b] |
|  | 1.00 | 2/4 | 6/8[b] |
|  | 2.00 | 0/4 | 0/8 |
|  | 4.00 | 0/4 | 0/8 |
|  | 6.00 | nd | 0/8 |
|  | 24.00 | nd | 0/8 |
| 122 | 0.25 | 3/4 | 1/8 |
|  | 0.50 | 3/4 | 3/8 |
|  | 1.00 | 4/4 | 3/8 |
|  | 2.00 | 1/4 | 3/8 |
|  | 4.00 | 1/4 | 3/8 |
|  | 6.00 | nd | 0/8 |
|  | 24.00 | nd | 0/8 |
| 123 | 0.25 | 3/4 | 0/8[c] |
|  | 0.50 | 3/4 | 0/8 |
|  | 1.00 | 3/4 | 0/8 |
|  | 2.00 | 2/4 | 0/8 |
|  | 4.00 | 0/4 | 0/8[c] |
|  | 24.00 | nd | 0/8 |
| 125 | 0.25 | 1/4 | 0/8 |
|  | 0.50 | 0/4 | 0/8 |
|  | 1.00 | 1/4 | 0/8 |
|  | 2.00 | 0/4 | 1/8 |
|  | 4.00 | 0/4 | 1/8 |
|  | 6.00 | nd | 1/8 |
|  | 8.00 | nd | 0/8 |
|  | 24.00 | nd | 0/8 |
| 130 | 0.25 | 4/4 | 0/8 |
|  | 0.50 | 3/4 | 0/8 |
|  | 1.00 | 2/4 | 0/8 |
|  | 2.00 | 0/4 | 0/8 |
|  | 4.00 | 0/4 | 0/4 |
|  | 6.00 | nd | 0/8 |
|  | 8.00 | nd | 0/8 |
|  | 24.00 | nd | 0/8 |
| 131 | 0.25 | 4/4 | 0/8[c] |
|  | 0.50 | 3/4 | 0/8 |
|  | 1.00 | 4/4 | 0/8 |
|  | 2.00 | 2/4 | 0/8 |
|  | 4.00 | 2/4 | 0/8 |
|  | 6.00 | nd | 0/8 |
|  | 8.00 | nd | 0/8 |
|  | 24.00 | nd | 0/8 |

[a]For definitions refer to Tables III, IV and V.
[b]Wet dog shakes.
[c]Exhibited hyperactivity.

TABLE VII

Intraperitoneal Evaluation of Compounds 113 and 115 in Rats

| Compound | Time, h | Dose, mg/kg | MES[a] | Dose, mg/kg | Tox[b] |
|---|---|---|---|---|---|
| 113 | 0.25 | 6.0 | 3/4 | 220 | 0/8 |
|  | 0.50 |  | 2/4 |  | 0/8 |
|  | 1.00 |  | 3/4 |  | 1/8 |
|  | 2.00 |  | 0/4 |  | 4/8 |
|  | 6.00 |  | nd[c] |  | 0/8 |
|  | 24.00 |  | nd[c] |  | 0/8 |
|  | 0.25 | 4.8 | 3/4 | 180 | nd[c] |
|  | 0.50 |  | 3/4 |  | nd[c] |
|  | 1.00 |  | 2/4 |  | nd[c] |
|  | 2.00 |  | nd[c] |  | 2/4 |
|  | 4.00 |  | nd[c] |  | 1/8 |
| 115 | 0.25 | 4.0 | 2/4 |  | nd[c] |
|  | 0.50 |  | 3/4 |  |  |
|  | 1.00 |  | 3/4 |  |  |
|  | 2.00 |  | 2/4 |  |  |
|  | 0.50 | 2.0 | 1/4 |  | nd[c] |
|  | 1.00 |  | 1/4 |  |  |

[a]Number of animals protected from electroshock seizures/numbers of animals tested.
[b]Number of animals exhibiting neurotoxicity/number of animals tested.
[c]nd = not determined.

TABLE VIII

Special Intraperitoneal Rat Quantitation Data for Compounds 113 and 115.

| Compound | Time, h | Dose, mg/kg | MES[a] | ED50[c] |
|---|---|---|---|---|
| 113 | 0.25 | 1.2 | 0/8 | 4.0 |
|  |  | 3.6 | 5/8 | (2.4–5.6) |
|  |  | 4.5 | 3/8 |  |
| 115 | 0.50 | 7.0 | 7/8 | 2.95 |
|  |  | 1.0 | 0/8 | (2.2–4.1) |
|  |  | 2.0 | 3/8 |  |
|  |  | 3.0 | 3/8 |  |
|  |  | 3.5 | 4/8 |  |
|  |  | 4.0 | 7/8 |  |

| Compound | Time, h | Dose, mg/kg | Tox[b] | ED50[c] | [d]PI, MES |
|---|---|---|---|---|---|
| 13 | 2.00 | 100 | 0/8 | 269.9 | 67.4 |
|  |  | 180 | 2/8 | (198.3–451.4) |  |
|  |  | 220 | 4/8 |  |  |
|  |  | 440 | 6/8 |  |  |
| 15 | 0.25–24 | 8 | 0/2 | >64 | >21.7 |
|  |  | 16 | 0/2 |  |  |
|  |  | 32 | 0/2 |  |  |
|  |  | 64 | 0.2 |  |  |

[a]Number of animals protected from electroshock seizures/number of animals tested.
[b]Number of animals exhibiting neurotoxicity/number of animals tested.
[c]ED50 and TD50 values are in milligrams/kilogram of test drug delivered intraperitoneally.
[d]PI = protective index (TD50/MES ED50).
Numbers in parentheses are 95% confidence interval.

For compounds which are water soluble (as are the majority of compounds included in this application), the ADD program provides an initial oral evaluation in rats, identical to the phase I tests previously indicated for mice, except that mice are given the candidate drug by intraperitoneal injection. This oral screen is designated as phase VI.

As a result of the favorable protective indices, compounds 12 and 27 were evaluated for oral activity in rats. Also included was the p-fluorobenzylamine derivative, 21 and dimedone 36. This data is shown in Table IX.

TABLE IX

Phase VI Oral Rat Data

| Compound | Dose, mg/kg | Time, h | MES[a] | Tox[b] | ED50[c] | TD50[d] | PI[e] |
|---|---|---|---|---|---|---|---|
| 12 | 50 | 0.25 | 2/4 | 0/4 | 26.75 | >500 | 18.69 |
|  |  | 0.50 | 4/4 | 0/4 | (16.30–38.10) | (nd) |  |
|  |  | 1.00 | 3/4 | 0/4 |  |  |  |
|  |  | 2.00 | 2/4 | 0/4 |  |  |  |
|  |  | 4.00 | 2/4 | 0/4 |  |  |  |
| 21 | 50 | 0.25 | 2/4 | 0/4 | 49.26 | >230 | 4.70 |
|  |  | 0.50 | 2/4 | 0/4 | (34.00–77.69) | (nd) |  |
|  |  | 1.00 | 1/4 | 0/4 |  |  |  |
|  |  | 2.00 | 2/4 | 0/4 |  |  |  |
|  |  | 4.00 | 3/4 | 0/4 |  |  |  |
| 27 | 10 | 0.25 | 3/4 | 0/4 | 5.79 | >380 | 65.63 |
|  |  | 0.50 | 4/4 | 0/4 | (3.98–7.38) | (nd) |  |
|  |  | 1.00 | 4/4 | 0/4 |  |  |  |
|  |  | 2.00 | 4/4 | 0/4 |  |  |  |
|  |  | 4.00 | 3/4 | 0/4 |  |  |  |
|  | 6 | 0.25 | nd | nd |  |  |  |
|  |  | 0.50 | 3/4 | 0/4 |  |  |  |
|  |  | 1.00 | 2/4 | 0/4 |  |  |  |
|  |  | 2.00 | 1/4 | 0/4 |  |  |  |
| 36 | 60 | 0.25 | 3/4 | 0/4 | 30.13 | >250 | 8.30 |
|  |  | 0.50 | 3/4 | 0/4 | (14.91–54.08) | (nd) |  |
|  |  | 1.00 | 0/4 | 0/4 |  |  |  |
|  |  | 2.00 | 0/4 | 0/4 |  |  |  |
|  |  | 4.00 | 0/4 | 0/4 |  |  |  |
| 107 | 50 | 0.25 | 2/4 | 0/4 |  |  |  |
|  |  | 0.50 | 1/4 | 0/4 |  |  |  |
|  |  | 1.00 | 3/4 | 0/4 |  |  |  |
|  |  | 2.00 | 2/4 | 0/4 |  |  |  |
|  |  | 4.00 | 1/4 | 0/4 | 4.00 | nd | nd |

TABLE IX-continued

Phase VI Oral Rat Data

| Compound | Dose, mg/kg | Time, h | MES[a] | Tox[b] | ED50[c] | TD50[d] | PI[e] |
|---|---|---|---|---|---|---|---|
| 109 | 50 | 0.25 | 4/4 | 0/4 | | | |
|  |  | 0.50 | 2/4 | 0/4 | | | |
|  |  | 1.00 | 2/4 | 0/4 | | | |
|  |  | 2.00 | 1/4 | 0/4 | | | |
|  |  | 4.00 | 1/4 | 0/4 | | | |
| 112 | 50 | 0.25 | 4/4 | 0/4 | | | |
|  |  | 0.50 | 4/4 | 0/4 | | | |
|  |  | 1.00 | 4/4 | 0/4 | | | |
|  |  | 2.00 | 4/4 | 0/4 | | | |
|  |  | 4.00 | 4/4 | 0/4 | | | |
| 113 | 50 | 0.25 | 3/4 | 0/4 | | | |
|  |  | 0.50 | 4/4 | 0/4 | | | |
|  |  | 1.00 | 4/4 | 0/4 | | | |
|  |  | 2.00 | 4/4 | 0/4 | | | |
|  |  | 4.00 | 4/4 | 0/4 | | | |
| 115 | 50 | 0.25 | 3/4 | 0/4 | | | |
|  |  | 0.50 | 4/4 | 0/4 | | | |
|  |  | 1.00 | 4/4 | 0/4 | | | |
|  |  | 2.00 | 4/4 | 0/4 | | | |
|  |  | 4.00 | 4/4 | 0/4 | | | |
| 116 | 50 | 0.25 | 4/4 | 0/4 | | | |
|  |  | 0.50 | 4/4 | 0/4 | | | |
|  |  | 1.00 | 4/4 | 0/4 | | | |
|  |  | 2.00 | 4/4 | 0/4 | | | |
|  |  | 4.00 | 4/4 | 0/4 | | | |
| 119 | 50 | 0.25 | 4/4 | 0/4 | | | |
|  |  | 0.50 | 3/4 | 0/4 | | | |
|  |  | 1.00 | 4/4 | 0/4 | | | |
|  |  | 2.00 | 4/4 | 0/4 | | | |
|  |  | 4.00 | 4/4 | 0/4 | | | |
| 121 | 50 | 0.25 | 3/4 | 0/4 | | | |
|  |  | 0.50 | 3/4 | 0/4 | | | |
|  |  | 1.00 | 4/4 | 0/4 | | | |
|  |  | 2.00 | 4/4 | 0/4 | | | |
| 122 | 50 | 0.25 | 3/4 | 0/4 | | | |
|  |  | 0.50 | 4/4 | 0/4 | | | |
|  |  | 1.00 | 3/4 | 0/4 | | | |
|  |  | 2.00 | 4/4 | 0/4 | | | |
| 123 | 50 | 0.25 | 4/4 | 0/4 | | | |
|  |  | 0.50 | 4/4 | 0/4 | | | |
|  |  | 1.00 | 4/4 | 0/4 | | | |
|  |  | 2.00 | 4/4 | 0/4 | | | |
|  |  | 4.00 | 4/4 | 0/4 | | | |
| 124 | 50 | 0.25 | 4/4 | 0/4 | | | |
|  |  | 0.50 | 4/4 | 0/4 | | | |
|  |  | 1.00 | 4/4 | 0/4 | | | |
|  |  | 2.00 | 4/4 | 0/4 | | | |
|  |  | 4.00 | 3/4 | 0/4 | | | |
| 125 | 50 | 0.25 | 4/4 | 0/4 | | | |
|  |  | 0.50 | 4/4 | 0/4 | | | |
|  |  | 1.00 | 4/4 | 0/4 | | | |
|  |  | 2.00 | 4/4 | 0/4 | | | |
|  |  | 4.00 | 4/4 | 0/4 | | | |
| 126 | 50 | 0.25 | 2/4 | 0/4 | | | |
|  |  | 0.50 | 3/4 | 0/4 | | | |
|  |  | 1.00 | 3/4 | 0/4 | | | |
|  |  | 2.00 | 3/4 | 0/4 | | | |
|  |  | 4.00 | 2/4 | 0/4 | | | |
| 127 | 50 | 0.25 | 1/4 | 0/4 | | | |
|  |  | 0.50 | 2/4 | 0/4 | | | |
|  |  | 1.00 | 4/4 | 0/4 | | | |
|  |  | 2.00 | 2/4 | 0/4 | | | |
|  |  | 4.00 | 1/4 | 0/4 | | | |
| 130 | 50 | 0.25 | 1/4 | 0/4 | | | |
|  |  | 0.50 | 1/4 | 0/4 | | | |
|  |  | 1.00 | 2/4 | 0/4 | | | |
|  |  | 2.00 | 3/4 | 0/4 | | | |
|  |  | 4.00 | 1/4 | 0/4 | | | |
| 131 | 50 | 0.25 | 4/4 | 0/4 | | | |
|  |  | 0.50 | 4/4 | 0/4 | | | |
|  |  | 1.00 | 4/4 | 0/4 | | | 2.004/40/4 |
| 138 | 50 | 0.25 | 0/4 | 0/4 | | | |
|  |  | 0.50 | 0/4 | 0/4 | | | |
|  |  | 1.00 | 0/4 | 0/4 | | | |

TABLE IX-continued

Phase VI Oral Rat Data

| Compound | Dose, mg/kg | Time, h | MES[a] | Tox[b] | ED50[c] | TD50[d] | PI[e] |
|---|---|---|---|---|---|---|---|
|  |  | 2.00 | 2/4 | 0/4 |  |  |  |
|  |  | 4.00 | 0/4 | 0/4 |  |  |  |
| 142 | 50 | 0.25 | 0/4 | 0/4 |  |  |  |
|  |  | 0.50 | 0/4 | 0/4 |  |  |  |
|  |  | 1.00 | 0/4 | 0/4 |  |  |  |
|  |  | 2.00 | 0/4 | 0/4 |  |  |  |
|  |  | 4.00 | 1/4 | 0/4 |  |  |  |
| 144 | 50 | 0.25 | 0/4 | 0/4 |  |  |  |
|  |  | 0.50 | 0/4 | 0/4 |  |  |  |
|  |  | 1.00 | 3/4 | 0/4 |  |  |  |
|  |  | 2.00 | 1/4 | 0/4 |  |  |  |
|  |  | 4.00 | 4/4 | 0/4 |  |  |  |
| 146 | 50 | 0.25 | 1/4 | 0/4 |  |  |  |
|  |  | 0.50 | 3/4 | 0/4 |  |  |  |
|  |  | 1.00 | 4/4 | 0/4 |  |  |  |
|  |  | 2.00 | 4/4 | 0/4 |  |  |  |
|  |  | 4.00 | 2/4 | 0/4 |  |  |  |
| 147 | 50 | 0.25 | 3/4 | 0/4 |  |  |  |
|  |  | 0.50 | 4/4 | 0/4 |  |  |  |
|  |  | 1.00 | 2/4 | 0/4 |  |  |  |
|  |  | 2.00 | 1/4 | 0/4 |  |  |  |
|  |  | 4.00 | 1/4 | 0/4 |  |  |  |
| 148 | 50 | 0.25 | 0/4 | 0/4 |  |  |  |
|  |  | 0.50 | 2/4 | 0/4 |  |  |  |
|  |  | 1.00 | 2/4 | 0/4 |  |  |  |
|  |  | 2.00 | 2/4 | 0/4 |  |  |  |
|  |  | 4.00 | 3/4 | 0/4 |  |  |  |
| 149 | 50 | 0.25 | 4/4 | 0/4 |  |  |  |
|  |  | 0.50 | 4/4 | 0/4 |  |  |  |
|  |  | 1.00 | 3/4 | 0/4 |  |  |  |
|  |  | 2.00 | 1/4 | 0/4 |  |  |  |
|  |  | 4.00 | 1/4 | 0/4 |  |  |  |
| 150 | 50 | 0.25 | 2/4 | 0/4 |  |  |  |
|  |  | 0.50 | 2/4 | 0/4 |  |  |  |
|  |  | 1.00 | 3/4 | 0/4 |  |  |  |
|  |  | 2.00 | 1/4 | 0/4 |  |  |  |
|  |  | 4.00 | 2/4 | 0/4 |  |  |  |
| 151 | 50 | 0.25 | 3/4 | 0/4 |  |  |  |
|  |  | 0.50 | 1/4 | 0/4 |  |  |  |
|  |  | 1.00 | 1/4 | 0/4 |  |  |  |
|  |  | 2.00 | 2/4 | 0/4 |  |  |  |
|  |  | 4.00 | 0/4 | 0/4 |  |  |  |
| 152 | 50 | 0.25 | 0/4 | 0/4 |  |  |  |
|  |  | 0.50 | 1/4 | 0/4 |  |  |  |
|  |  | 1.00 | 1/4 | 0/4 |  |  |  |
|  |  | 2.00 | 3/4 | 0/4 |  |  |  |
|  |  | 4.00 | 2/4 | 0/4 |  |  |  |
| 153 | 50 | 0.25 | 0/4 | 0/4 |  |  |  |
|  |  | 0.50 | 2/4 | 0/4 |  |  |  |
|  |  | 1.00 | 3/4 | 0/4 |  |  |  |
|  |  | 2.00 | 3/4 | 0/4 |  |  |  |
|  |  | 4.00 | 1/4 | 0/4 |  |  |  |
| 154 | 50 | 0.25 | 0/4 | 0/4 |  |  |  |
|  |  | 0.50 | 0/4 | 0/4 |  |  |  |
|  |  | 1.00 | 0/4 | 0/4 |  |  |  |
|  |  | 2.00 | 0/4 | 0/4 |  |  |  |
|  |  | 4.00 | 0/4 | 0/4 |  |  |  |
| phenytoin |  |  |  |  | 29.80 (21.9–38.9) | >3000[e] | >100 |
| carbamazepine |  |  |  |  | 8.50 (3.39–10.5) | 813[e] (489–1234) | 95.7 |
| valproate |  |  |  |  | 490 (351–728) | 280[e] (191–353) | 0.57 |

[a]Maximal electroshock test (refer to Table III for definition).
[b]Toxicity (refer to Table IV).
[c]Refer to Table III for definition.
[d]Tox data based on ataxia.
nd = not determined.

As previously noted in mice, 12 and 27 displayed excellent protection (18.69 and 65.63 respectively). The toxicity evaluation for the commercial agents as previously indicated was based on the onset of ataxia. None of the compounds in this report displayed ataxia. Compound 12 was subjected to a special ip rate screening evaluation (Table X). No toxicity was noted at 100 mg/kg throughout the four hour evaluation.

TABLE X

Special ip Rat Screening for Methyl 4-(benzyl)amino-6-methyl-2-oxocyclohex-3-en-1-oate (12)

| Dose, mg/kg | Time, h | Activity MES[a] | Tox[b] |
|---|---|---|---|
| 100 | 0.25 | 4/4 | 0/4 |
|  | 0.50 | 4/4 | 0/4 |
|  | 1.00 | 4/4 | 0/4 |
|  | 2.00 | 4/4 | 0/4 |
|  | 4.00 | 3/4 | 0/4 |

[a]Maximal electroshock test (refer to Table III for definition).
[b]Toxicity (refer to Table III).

TABLE X-A

Intraperitoneal (ip) toxicity of Compounds 27, 7 and 36 in rats (100 mg/kg).

| Time, h | Comp. 27 | #Resp/ # Tested[a] | Comp. 7 | # Resp/ # Tested[a] | Comp. 36 | # Resp/ # Tested[a] |
|---|---|---|---|---|---|---|
| 0.25 |  | 0/8 |  | 1/8 |  | 5/8 |
| 0.50 |  | 3/8 |  | 5/8 |  | 7/8 |
| 1.00 |  | 6/8 |  | 0/8 |  | 6/8 |
| 2.00 |  | 7/8 |  | 0/8 |  | 6/8 |
| 4.00 |  | 2/8 |  | 0/8 |  | 3/8 |
| 6.00 |  | 1/8 |  | 0/8 |  | 3/8 |
| 8.00 |  | 0/8 |  | nd[b] |  | nd[b] |
| 24.00 |  | 2/8[c] |  | 0/8 |  | 0/8 |

[a]Number of animals displaying neurotoxicity/number of animals tested.
[b]nd = not determined.
[c]2 animals died.

Figure 1B:
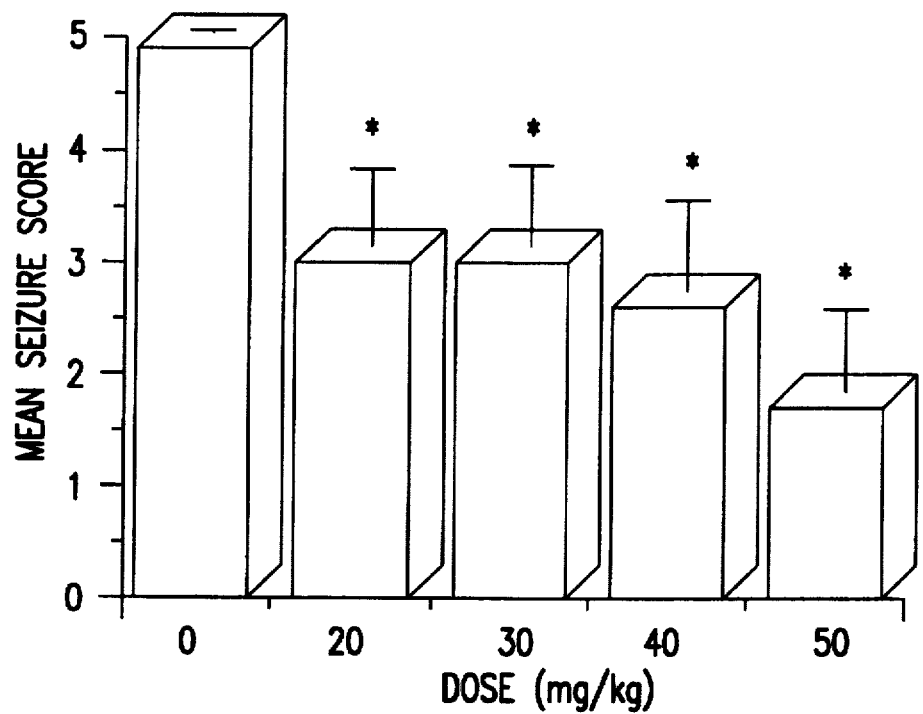

Corneal kindling studies were performed in our laboratories on 12 and 27 and the results are shown in Tables XI and XII and FIGS. 1A and 1B. Comparative data for the commercial products are included. Seizures evoked in electroshock-kindled rats provide a suitable model consistent with complex partial seizures evolving into generalized motor seizures in humans.

TABLE XI

Corneal Kindling Rat Data[a]

| Compound | Route | Time of test, h | ED50 | 95% Confidence interval |
|---|---|---|---|---|
| 12 | po | 0.5 | 41.9 | 34.0–51.6 |
| 27 | po | 0.5 | 31.2 | 18.2–64.2 |
| clonazepam[b] | po | 1 | 0.70 | 0.53–1.02 |
| carbamazepine[b] | po | 1 | 28.90 | 7.73–75.59 |
| phenytoin[b] | po | 0.5 | >100 |  |
| phenytoin[b] | ip | 0.5 | 48.25 | 24.57–78.36 |
| valproate[b] | po | 0.5 | 117.41 | 67.98–189.02 |

[a]Rats kindled to Stage 5. Endpoint was reduction from Stage 5 to Stage 4.
[b]Data provided by the ADD Program.

TABLE XII

Rat Kindling Data for Methyl 4-benzylamino-6-methyl-2-oxocyclohex-3-en-1-oate (12) and Methyl 4-(p-chloro)phenylamino-2-oxocyclohex-3-en-1-oate (27)

| Compound | Dose, mg/kg | % Reduction | Ave. seizure score[a] | S.E.M.[b] | N[c] |
|---|---|---|---|---|---|
| 12 | 50 | 17 |  |  | 6 |
|  | 60 | 23 |  |  | 6 |
|  | 75 | 75 |  |  | 46 |
| 27 | 0 | 0 | 4.9 | 0.042 | 57 |
|  | 20 | 40 | 3.0 | 0.700 | 12 |
|  | 30 | 40 | 3.0 | 0.760 | 11 |
|  | 40 | 49 | 2.6 | 0.880 | 7 |
|  | 50 | 87 | 1.7 | 0.890 | 9 |

[a]Ranking system: 0 = no effect; 1 = immobility; 2 = facial clonus, head nodding; 3 = facial clonus and rearing; 4 = forelimb clonus and rearing; 5 = forelimb clonus and falling
[b]Standard error of the mean.
[c]Number of animals tested.

Compound 27 provided an ED50 of 31.2 mg/kg. It should be noted that phenytoin was inactive in this test via the oral route. The ED50 data for 27 of 31.2 mg/kg compares favorably with carbamazepine (28.90 mg/kg).

Compounds 12 and 27 were evaluated in our laboratory for suppression of amygdala kindled seizures. This data is shown in Table XIII and indicated no significant activity.

TABLE XIII

Effect of compounds 27 and 12 on Amygdala Kindled Seizures[a]

| | Baseline[b,c] (0.5% MC) | 27[c] (350 mg/kg) | Baseline[b,c] (0.5% MC) | 12[c] (500 mg/kg) |
|---|---|---|---|---|
| Afterdischarge |  |  |  |  |
| Amygdala: |  |  |  |  |
| Duration(s) | 76.7 | 79.8 | 78.6 | 73.9 |
|  | (±18.7) | (±19.0) | (±13.1) | (±15.5) |
| Cortex: |  |  |  |  |
| Latency(s) | 2.1 | 2.7 | 1.3 | 2.8 |
|  | (±0.5) | (±0.6) | (±0.3) | (±1.3) |
| Duration(s) | 83.4 | 79.6 | 92.0 | 78.9 |
|  | (±15.2) | (±17.8) | (±16.2) | (±9.4) |
| Behavioral Seizure: |  |  |  |  |
| Latency(s) | 2.1 | 2.1 | 2.0 | 2.1 |
|  | (±0.2) | (±0.1) | (±0.2) | (±0.1) |

TABLE XIII-continued

Effect of compounds 27 and 12 on Amygdala Kindled Seizures[a]

|                  | Baseline[b,c] (0.5% MC) | 27[c] (350 mg/kg) | Baseline[b,c] (0.5% MC) | 12[c] (500 mg/kg) |
|------------------|-------------------------|-------------------|-------------------------|--------------------|
| Duration(s)      | 90.0 (±11.7)            | 82.3 (±17.0)      | 100.0 (±18.0)           | 79.5 (±10.8)       |
| Forelimb Clonus: |                         |                   |                         |                    |
| Latency(s)       | 5.6 (±3.0)              | 9.2 (±6.8)        | 8.7 (±4.3)              | 9.3 (±4.1)         |
| Duration(s)      | 54.8 (±8.2)             | 45.3 (±7.2)       | 41.7 (±17.2)            | 44.2 (±13.2)       |
| Seizure Stage:   | 5.0 (±0.0)              | 5.0 (±0.0)        | 5.0 (±0.0)              | 5.0 (±0.0)         |

[a]See experimental section for details.
[b]MC = methyl cellulose.
[c]Data in parenthesis represents the standard deviation based on N = 8 animals for 27 and N = 6 animals for 12.

Both 12 and 27 were evaluated in Phase V of the ADD Program evaluation scheme. Phase V provides quantification against bicuculline, picrotoxin, pentylenetetrazol, and strychnine. This screen provides information on the mechanism of action of the anticonvulsant activity. Bicuculline, picrotoxin, and strychnine correspond to GABA inhibitory function, chloride channel inhibition and inhibition by glycine respectively. Compound 12 was uniformly inactive in all tests at doses of 12.5, 25, 50 and 100 mg/kg. Compound 27 was also uniformly inactive in these tests. While not protecting the animals, 27, contrary to other commercial anticonvulsants (e.g., phenytoin), did not lower the threshold to these chemostimulants. In addition, 27 was inactive in the benzodiazepine receptor binding evaluation, the GABA receptor binding test and the adenosine uptake assay. In view of the recent reports that 5-fluoro-4-oxopentanoic acid and 3,5-dioxocyclohexanecarboxylic acid inhibit GABA aminotransferase and were classified as "Class IV" inactivators, the starting β-hydroxyketones were tested and found to be inactive in phase I evaluations. This fact, together with the rapid onset of action of 12 and 27 would preclude their acting as prodrugs. From the results of the test data set out above, it appears that the presence or absence of several structures may effect anticonvulsant activity.

For anticonvulsant activity, primary amines must be employed as pyrrolidine and morpholine analogs, i.e., where instead of a primary amine adjacent to $R^3$, the nitrogen is part of a heterocyclic radical, were found to be uniformly inactive. It appears that the primary amine should be attached directly, or through a methylene, ethylene or amino bridge, to an aromatic ring. The condensation of β-hydroxyketo ester 3 ($R=CO_2CH_3$; $R^1=CH_3$; $R^2=H$) with N-aminomorpholine produced the two isomers, 33 and 34. However, neither was active in phase I evaluations. In addition, it was observed that in proceeding through the homologous series from the active unsubstituted benzylamine analog 12 to the unsubstituted phenylamine compound 24, activity was lost. Similarly, other unsubstated phenylamines, 17 and 29, were inactive.

The anticonvulsant activity data further showed that while a methyl or dimethyl functionality at position 6 increases anticonvulsant activity, phenyl substitution 11 produces inactive compounds.

The anticonvulsant activity when there was a ester functionality at position 1 was found to vary widely. Two dimedone analogs 19 and 36 have also proved to be potent anticonvulsants. Phase II (Table V) and Phase VI (Table VI) data for 36 indicates that the protective index in mice is modest, while in rats anticonvulsant activity is lost after 1 hour. Thus, it appears that for maximum sustained activity and safety, the carbomethoxy function should be present.

In view of the highly active 12, a systematic evaluation of the electronic and steric effects involved in para substitution was undertaken. The substituted benzylamines 16, 17, 18, 20 and 21 provided only a slight modification in activity compared with 12, with only 21 providing any significant activity in Phase II evaluation, establishing that activity may reside in the +σ, +π quadrant. The fact that the enaminone of aniline, 24, the starting compound in our analysis was inactive in anticonvulsant evaluations was unexpected. Nevertheless, with the exceptions of 32 (comparable to inactive 18 in the benzylamine series) and 35, anticonvulsant activity was observed in the series, i.e., 26, 27, 28, 29, 30, 31, 32 and 35. Thus the conclusion that anticonvulsant activity can be enhanced by para substitution to the +σ, +π quadrant as well as the −σ, +π quadrant appears valid.

Figure 2A:
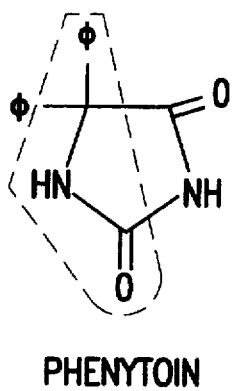
FIGS. 2A, 2B, and 2C give proposed "fingerprint" regions of the active sites in the enaminones of the present invention.
Figure 2B:
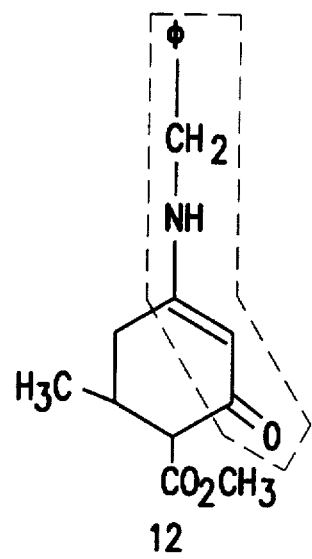
Figure 2C:
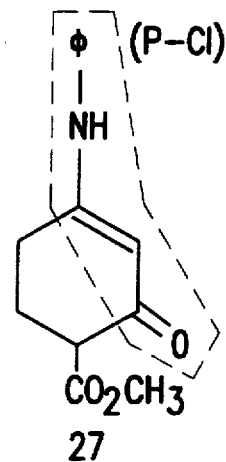
Figure 3A:
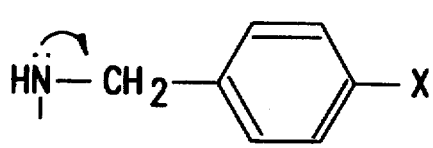
FIGS. 3A and 3B show the effect of substituted benzylamines and anilines.
Figure 3B:
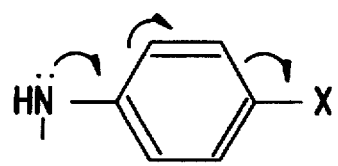

Due to the similarity in anticonvulsant spectrum to phenytoin, it seemed logical to depict each of the active enaminones, 12 and 27, against that of phenytoin. This is shown in FIGS. 2A, 2B and 2C. Furthermore, the lack of enhanced anticonvulsant activity in the benzylamine series may be due to the lack of a −I effect with the para substituents due to the methylene bridge which effectively blocks this electronic contribution. This is shown in FIGS. 3A and 3B. As noted by Topliss, para-fluoro substitution produces a minimal change in σ and π effects compared to the unsubstituted compound. This is borne out in the anticonvulsant activity of 21. Steric effects in the benzylamine series cannot be overlooked. FIGS. 2A, 2B and 2C indicates an increased distance from the phenyl ring to the carbonyl group of 12 compared to phenytoin and 27.

The aniline series bears out the conclusion that a −I effect enhances activity, and that strong +π groups enhance activity. Comparing para-chlorobenzylamine 16 to para-chlorophenylamine 27, para-methylbenzylamine 17 to para-methylaniline 28, para-nitro-benzylamine 20 to para-nitroaniline 29, it is clear that activity is enhanced in all cases. In addition, the para hydroxy phenyl analog, 35, is inactive which parallels the metabolic inactivation of phenytoin. Thus, the active anticonvulsant region of the enaminones can tentatively be outlined as indicated in FIGS. 2A, 2B, and 2C.

While the present invention has been described in connection with a specific embodiment, it is understood that modifications and variations may be resorted to without departing from the spirit and scope of the invention. As those

We claim:
1. An enaminone having the formula

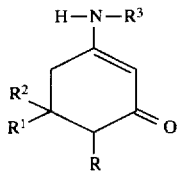

wherein

R is COOCH$_3$;

R$^1$ is CH$_3$;

R$^2$ is H; and

R$^3$ is selected from the group consisting of C$_6$H$_4$(p-Cl) and CH$_2$C$_6$H$_5$.

2. The enaminone of claim 1, wherein R$_3$ is C$_6$H$_4$(p-Cl).

3. A pharmaceutical composition for alleviating convulsive seizures comprising a therapeutically effective amount of an enaminone of claim 1 in a pharmaceutically acceptible vehicle.

4. A method of treating a patient suffering from convulsive seizures, said method comprising administering to said patient a pharmaceutical composition according to claim 3.

UNITED STATES PATENT AND TRADEMARK OFFICE
CERTIFICATE OF CORRECTION

PATENT NO. : 5,616,615
DATED : 1 April 1997
INVENTOR(S) : Kenneth R. SCOTT et al.

It is certified that error appears in the above-indentified patent and that said Letters Patent is hereby corrected as shown below:

| Column | Line | |
|---|---|---|
| 2 | 28 | Before "are" insert --$R^1, R^2, R^3, R^4$=H, alkyl or alkyl-aryl--. |
| 6 | 23 | Change "t0" to --10--. |
| Table I | 4 | Change "mp.°C." to --mp, °C$^b$--. |
| Table I | 13 | Change "173-174°g" to --173-174$^g$--. |
| Table I | 27 | Change "$C_6H_5$" to --$C_6H_3$--. |
|  | 28 | Change "$C_6H_5$" to --$C_6H_3$--. |
| 7-8 | 4 | Change "mp.°C." to --mp, °C$^b$--. |
| 7-8 | 11 | Change "$C_{15}H_{17}NO_5$" to --$C_{15}H_{17}NO_3$--. |
| 7-8 | 36 | Change "$C_6H_5(2',5'-(OCH_3)_2)$" to --$C_6H_3(2',5'-(OCH_3)_2)$--. |
| 7-8 | 16th line from bottom: | Change "93.5-95°" to --93.5-95$^e$--. |

UNITED STATES PATENT AND TRADEMARK OFFICE
CERTIFICATE OF CORRECTION

PATENT NO. : 5,616,615

DATED : 1 April 1997

INVENTOR(S) : Kenneth R. SCOTT et al.

It is certified that error appears in the above-indentified patent and that said Letters Patent is hereby corrected as shown below:

| Column | Line | |
|---|---|---|
| 9-10 | 4 | Change "mp.°C." to --mp, °C$^b$--. |
| 9-10 | 15 | Change " $^t$EtO Ac:MeOH (2:2:1)." to -- $^t$EtO Ac:Me$_2$CO:MeOH (2:2:1).--. |
| 11 | 35 | Change "10" to --100--; change "0.1  0.1  0.8  0.4" to --0/1  0/1  0/8  0/4--. |
| 11 | 36 | Change "1/1$^c$" to --1/1$^e$--. |
| 11 | 55,57,59,61 | Change "300$^c$" to --300$^e$--. |
| 12 | 13,16,19,20,22,25,27,28,31 | Change "300$^c$" to --300$^e$--. |
| 13 | 45 | Change "$^a$The" to --$^d$The--. |

Signed and Sealed this

Twenty-third Day of September, 1997

Attest:

BRUCE LEHMAN

Attesting Officer

Commissioner of Patents and Trademarks